US007940395B2

(12) United States Patent
Monkowski et al.

(10) Patent No.: US 7,940,395 B2
(45) Date of Patent: May 10, 2011

(54) METHOD AND APPARATUS FOR IDENTIFYING THE CHEMICAL COMPOSITION OF A GAS

(75) Inventors: Joseph R. Monkowski, Danville, CA (US); Barton Lane, Pleasanton, CA (US)

(73) Assignee: Pivotal Systems Corporation, Pleasanton, CA (US)

( * ) Notice: Subject to any disclaimer, the term of this patent is extended or adjusted under 35 U.S.C. 154(b) by 31 days.

(21) Appl. No.: 12/184,574

(22) Filed: Aug. 1, 2008

(65) Prior Publication Data

US 2009/0180113 A1    Jul. 16, 2009

Related U.S. Application Data

(60) Provisional application No. 61/020,457, filed on Jan. 11, 2008, provisional application No. 60/963,974, filed on Aug. 7, 2007.

(51) Int. Cl.
*G01N 21/00* (2006.01)
(52) U.S. Cl. ........................................ 356/437; 356/432
(58) Field of Classification Search .................. 356/437, 356/311, 326, 432, 442, 440, 303; 216/60, 216/67–71; 438/476; 427/569–570, 255.28
See application file for complete search history.

(56) References Cited

U.S. PATENT DOCUMENTS 7,052,943 B2    5/2006    Yamazaki et al.
2003/0129117 A1    7/2003    Mills

OTHER PUBLICATIONS

International Search Report and Written Opinion of PCT Application No. PCT/US08/72008, date of mailing Oct. 14, 2008, 10 pages total.

*Primary Examiner* — Gregory J Toatley
*Assistant Examiner* — Tri T Ton
(74) *Attorney, Agent, or Firm* — Kilpatrick Townsend & Stockton LLP

(57) ABSTRACT

Embodiments of the present invention relate to the analysis of the components of one or more gases, for example a gas mixture sampled from a semiconductor manufacturing process such as plasma etching or plasma enhanced chemical vapor deposition (PECVD). Particular embodiments provide sufficient power to a plasma of the sample, to dissociate a large number of the molecules and molecular fragments into individual atoms. With sufficient power (typically a power density of between 3-40 $W/cm^3$) delivered into the plasma, most of the emission peaks result from emission of individual atoms, thereby creating spectra conducive to simplifying the identification of the chemical composition of the gases under investigation. Such accurate identification of components of the gas may allow for the precise determination of the stage of the process being performed, and in particular for detection of process endpoint.

38 Claims, 12 Drawing Sheets

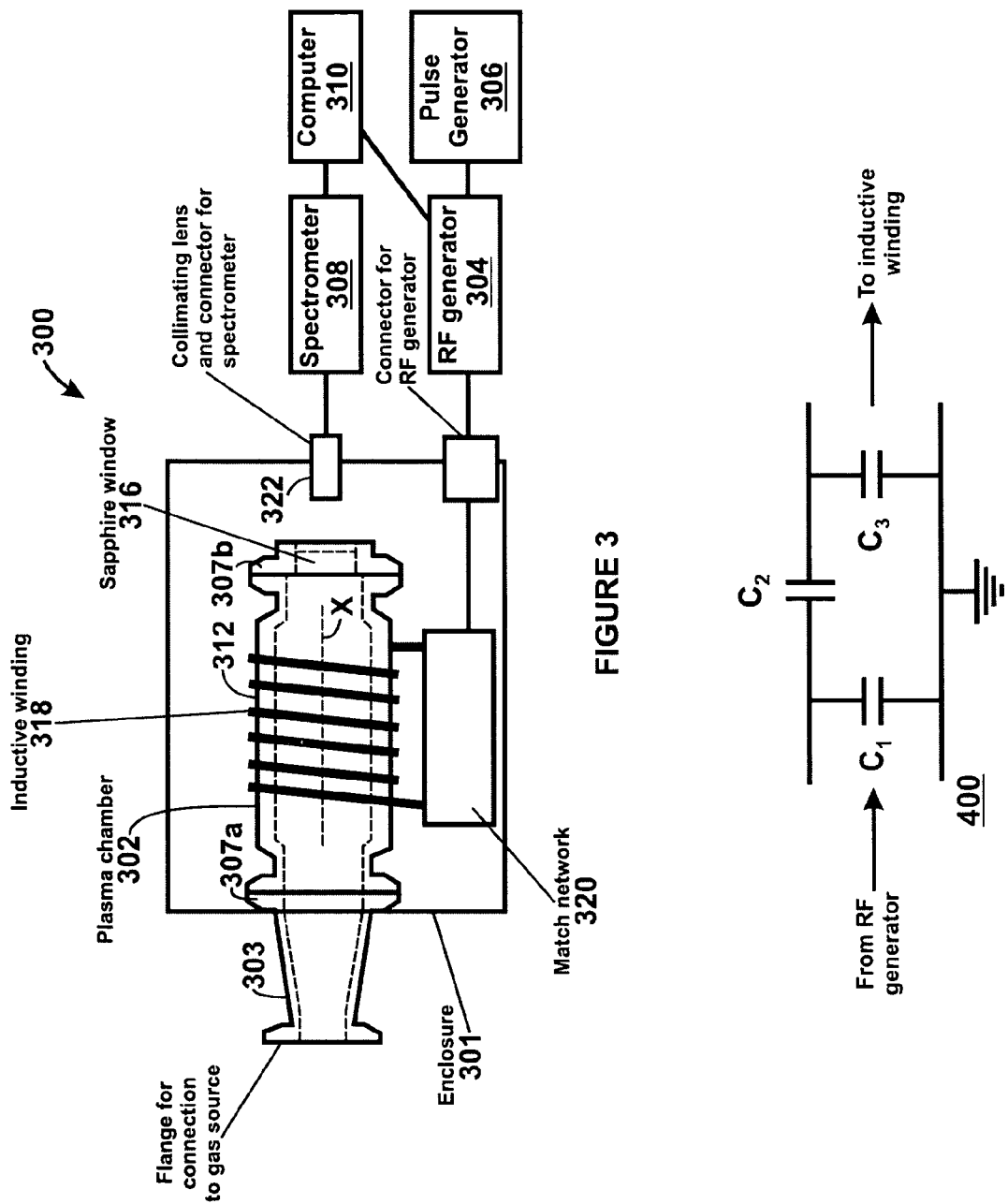

| Observed Wavelength Vac (nm) | Rel. Int. | Observed Wavelength Vac (nm) | Rel. Int. | Observed Wavelength Vac (nm) | Rel. Int. | Observed Wavelength Vac (nm) | Rel. Int. |
|---|---|---|---|---|---|---|---|
| | | 551.9068 | 35 | 716.7520 | 200 | 1066.3896 | 120 |
| 201.162 | 30 | 562.3782 | 30 | 718.687 | 70 | 1069.7181 | 30 |
| 205.549 | 50 | | | 719.556 | 65 | 1073.0347 | 30 |
| 206.185 | 40 | 564.7178 | 90 | 719.588 | 30 | 1075.2329 | 60 |
| 206.618 | 30 | 566.7126 | 80 | | | 1078.7504 | 30 |
| 210.388 | 30 | 568.6061 | 120 | 722.8197 | 100 | | |
| | | 569.2084 | 100 | 723.7320 | 100 | 1078.9812 | 80 |
| 211.530 | 30 | 570.2687 | 90 | 723.781 | 60 | 1083.0057 | 140 |
| 212.479 | 100 | | | 725.2623 | 180 | 1084.6824 | 60 |
| 214.859 | 50 | 570.9991 | 160 | 727.7299 | 160 | 1087.177 | 30 |
| 220.867 | 110 | 574.9261 | 45 | | | 1087.2518 | 130 |
| 221.158 | 115 | 575.5221 | 45 | 728.482 | 40 | | |
| | | 575.5816 | 45 | 729.1181 | 400 | 1088.5783 | 30 |
| 221.243 | 110 | 576.4575 | 45 | 729.227 | 55 | 1088.8318 | 30 |
| 221.736 | 120 | | | 737.503 | 35 | 1098.2315 | 80 |
| 221.875 | 120 | 577.3746 | 70 | 740.7814 | 375 | 1098.5069 | 30 |
| 221.960 | 50 | 578.1987 | 70 | | | | |
| 229.174 | 35 | 579.4677 | 90 | 741.1123 | 200 | | |
| | | 579.9467 | 100 | 741.739 | 40 | | |
| 230.377 | 55 | 587.5392 | 40 | 741.7989 | 275 | | |
| 243.589 | 300 | | | 742.5542 | 425 | | |
| 243.951 | 65 | 595.0191 | 200 | 742.664 | 85 | | |
| 244.430 | 65 | 612.6716 | 90 | | | | |
| 245.286 | 70 | 613.3271 | 85 | 768.2381 | 200 | | |
| | | 613.3547 | 90 | 774.484 | 40 | | |
| 250.766 | 425 | 614.4187 | 100 | 780.2154 | 30 | | |
| 251.508 | 375 | | | 785.2127 | 30 | | |
| 251.6870 | 500 | 614.6716 | 100 | 792.0564 | 90 | | |
| 251.9960 | 350 | 615.6837 | 160 | | | | |
| 252.4867 | 425 | 623.9045 | 160 | 793.4531 | 120 | | |
| | | 624.0013 | 40 | 794.6186 | 140 | | |
| 252.9269 | 450 | 624.5540 | 125 | 797.2498 | 35 | | |
| 253.3142 | 110 | | | 803.7829 | 35 | | |
| 256.9411 | 85 | 624.6195 | 125 | 809.5400 | 70 | | |
| 257.7923 | 45 | 625.5918 | 180 | | | | |
| 263.2067 | 190 | 633.3705 | 45 | 823.2905 | 35 | | |
| | | 652.8412 | 45 | 844.6302 | 40 | | |
| 288.2424 | 1000 | 652.9002 | 45 | 850.3883 | 40 | | |
| 297.1222 | 55 | | | 850.4557 | 60 | | |
| 298.8517 | 150 | 655.7273 | 45 | 853.8510 | 40 | | |
| 300.7615 | 50 | 672.3709 | 100 | | | | |
| 302.0884 | 75 | 674.350 | 30 | 855.9131 | 120 | | |
| | | 685.0458 | 30 | 865.0830 | 50 | | |
| 390.5629 | 300 | 697.8447 | 80 | 873.0408 | 40 | | |
| 410.4094 | 70 | | | 874.4852 | 75 | | |
| 478.8328 | 50 | 700.5498 | 180 | 875.4413 | 100 | | |
| 479.3552 | 35 | 700.7815 | 180 | | | | |
| 479.3664 | 80 | 701.922 | 30 | 879.2803 | 35 | | |
| | | 701.9581 | 90 | 941.6089 | 100 | | |
| 494.8988 | 30 | 703.6843 | 250 | 1037.4111 | 30 | | |
| 500.7457 | 40 | | | 1058.8041 | 120 | | |
| 549.467 | 40 | 716.666 | 70 | 1060.6336 | 120 | | |

METHOD AND APPARATUS FOR IDENTIFYING THE CHEMICAL COMPOSITION OF A GAS

CROSS-REFERENCE TO RELATED APPLICATIONS

The instant nonprovisional patent application claims priority to U.S. Provisional Patent Application No. 60/963,974 filed Aug. 7, 2007, and to U.S. Provisional Patent Application No. 61/020,457 filed Jan. 11, 2008, both of which are incorporated by reference in their entireties herein for all purposes.

BACKGROUND

Integrated circuits or "ICs" have evolved from a handful of interconnected devices fabricated on a single chip of silicon to millions of devices. Current ICs provide performance and complexity far beyond what was originally imagined. In order to achieve improvements in complexity and circuit density (i.e., the number of devices capable of being packed onto a given chip area), the size of the smallest device feature, also known as the device "geometry", has become smaller with each generation of ICs. Semiconductor devices are now being fabricated with features less than a quarter of a micron across.

As merely an example, etching processes are often used to remove or partially remove a layer to form structures there from. Etching is often performed by an etching tool, such as a dry etcher or wet etcher. The wet etcher often includes a vessel that has an etchant chemical to selectively remove one material from another material. The dry etcher often includes a plasma source and treatment chamber. The dry etcher often uses gases such as fluorine bearing species and chlorine bearing species to remove semiconductor materials such as silicon, or metal such as aluminum, or dielectric material such as silicon oxide.

Much work has been done to use real-time metrology to characterize semiconductor manufacturing processes and the effect of these processes on the wafers being processed. In contrast to ex situ metrology, which allows detailed scrutiny of the wafer surface, real-time metrology requires in situ measurement, which rarely allows such a close investigation of the wafer. Consequently, one needs to measure parameters such as the power being delivered into a process chamber, or the gases inside a process chamber in order to make inferences about the state of the wafer.

Typical objectives of real-time metrology for semiconductor processes include identification of a particular wafer state, such as that point at which a particular thin film is fully etched in a plasma etch process (the end point); or characterization of key process parameters, such as the rate at which a thin film is being deposited or etched.

One approach to measuring a gas inside a process chamber is to use a spectrometer to measure the light emitted from the plasma inside the process chamber. Another approach to measuring the gas inside a process chamber is to use a system comprising a self-contained plasma chamber with a spectrometer to measure the light emitted from the self-contained plasma. For example, in using such a system, the self contained plasma chamber of the detection apparatus would be in fluid communication with the processing chamber, such that the gas from the processing chamber can flow and/or diffuse into the plasma chamber of the detector apparatus.

In both of these approaches, when the gas is excited by the self-contained plasma, a fraction of the gaseous particles, which can include atoms, molecules, and molecular fragments, will have one or more of their electrons excited to a higher-energy state. When these electrons fall back to their lower-energy states, photons, with energy equal to the energy lost by the electrons, are emitted from the gaseous particles. The energy of each of the photons is characteristic of the particle (atom, molecule, or molecular fragment) from which it was emitted.

Since the photon energy is characteristic of the gaseous particle from which it was emitted, and there is a one-to-one relationship between photon energy and wavelength (or frequency, which is inversely proportional to wavelength), measurement of the intensity of the emitted light as a function of wavelength can provide information on the gaseous particles present in the plasma, thus providing information on the chemical composition of the gas.

For example, FIG. 1 shows a conventional emission spectrum taken from a chamber having a plasma comprising air. The y-axis of FIG. 1 indicates the intensity of the emission (in arbitrary units), which generally increases with increasing concentration of the emitting particle in the gas mixture. The x-axis of FIG. 1 indicates the wavelength of the emission, measured in nanometers.

The spectrum of FIG. 1 is characteristic of nitrogen gas in molecular form, which is to be expected given that air comprises approximately 80% such molecular nitrogen. Apart from revealing the presence of molecular nitrogen, however, the emission spectrum of FIG. 1 provides relatively little information Specifically, in addition to nitrogen, air also contains approximately 20% oxygen. However, the spectrum of FIG. 1 lacks any meaningful indication of the presence of the oxygen.

This is because gas mixtures will typically contain many different molecules and/or atoms. Gases in molecular form in general produce spectra which consist of bands corresponding to electronic transitions, which are comprised of sub bands corresponding to transitions between vibrational states, and these sub-bands themselves comprise many individual lines corresponding to transitions between different rotational states. The finite resolution of the spectrometer blurs these many lines together into continuous bands. Although the spectrum for molecular nitrogen exhibits more bands than most molecules or molecular fragments, a typical spectrum of most gases in molecular form is still usually crowded with bands, which in general overlap from one gas component to another. This makes it difficult to ascertain the true chemical composition of the gas mixture utilizing conventional spectroscopic techniques when the gas mixture is dominated by gases in molecular form. By contrast, the emission spectrum of atoms tends to consist of isolated lines, many of which are sufficiently separated in wavelength that they can be resolved by conventional spectrometers.

Still another difficulty with the use of conventional spectroscopic techniques lies in the difficulty of associating the peaks of a spectrum to the particular molecules or molecular fragments. For example, the documentation of emission spectra from atoms is very detailed and comprehensive. An excellent source of information on the specific wavelengths that a particular atom emits, along with the relative intensity of the emission at each of the specific wavelengths, is available from the National Institute of Standards and Technology (NIST) at http://physics.nist.gov/PhysRefData/ASD/lines_form.html.

By contrast, the emission spectra from molecules or molecular fragments are much less well documented. Thus even if the emissions of a particular molecule or molecular fragment could be segregated from others in a spectrum, correlation of this information to a known component of the gas mixture would not be possible in many instances. The problem is exacerbated by the highly energetic state of the plasma, in which unstable molecules and molecular fragments can form and then dissociate in very short time scales.

Previous work has been carried out on atomic emission detectors for analytical techniques such as chromatography. Frequently, such detectors are used to vaporize and analyze liquids, often with large amounts of argon or another carrier gas added to the mixture. Although these approaches allow detection of atomic emission, they are designed to operate at atmospheric pressure, and are ill-suited for analysis of the gaseous environments inside of process chambers such as those used in the processing of semiconductor devices.

Another related analytical technique is Inductively Coupled Plasma-Optical Emission Spectroscopy (ICP-OES). This technique uses an ICP torch comprising concentrically arranged quartz tubes with a water-cooled RF coil. In conjunction with an argon carrier gas, the ICP torch creates a high temperature plasma (approximately 7,000K) that atomizes and excites the material to be analyzed. ICP-OES is frequently used for the analysis of trace metals. Because of the torch-like configuration, the high flow rate of the argon carrier gas, and the operation at atmospheric pressure, however, this technique is also unsuitable for analysis of the environments arising during the fabrication of semiconductor devices.

A final difficulty with the use of conventional spectroscopic techniques is in the strength of the signals that are to be observed. Specifically, as device size shrinks, the area of the material that is changed by the process being studied may represent only a very small fraction of the overall area. For example, in a typical step of etching a via with a plasma, the area of dielectric layer to be removed is only about 1% or less of the total area. Since conventional measurement techniques such as optical emission spectrometry (OES) or radio frequency (RF) measurements measure an overall plasma state, the effect from other interferences can overwhelm the signal of the measurement.

Silicon-containing dielectric films (such as silicon nitride, silicon dioxide, doped silicon dioxide, and low-k films) are commonly present in semiconductor devices. These silicon-containing dielectric films are first deposited as a blanket layer, and then removed in selected regions exposed by photolithography. Removal of the dielectric layer is accomplished by etching, which must be performed with high precision so as not to damage the material underlying the dielectric. The key to precise etching is to accurately determine the process endpoint—the point in time at which the silicon dioxide is no longer being removed.

Typically, however, the exposed area of the dielectric films being etched will be very small (for example a few percent or less of the total area), resulting in any signal associated with the endpoint of such etching being very small. The combination of (i) a small signal, (ii) obscuring of signals by multiple bands overlapping one another, and (iii) the difficulty of identifying the gas species associated with any particular emission, conventionally renders detection of the endpoint of the etching process very difficult.

From the above, it is seen that improved techniques, systems, and methods for analyzing gas mixtures and determining process endpoint, are desired

SUMMARY

Embodiments of the present invention relate to the analysis of the components of one or more gases, for example a gas mixture sampled from a semiconductor manufacturing process such as plasma etching or plasma enhanced chemical vapor deposition (PECVD). Embodiments in accordance with the present invention provide sufficient power to a plasma of the sample, to dissociate a large number of the molecules and molecular fragments into individual atoms. With sufficient power (typically a power density of between 3-40 W/cm$^3$) delivered into the plasma, most of the emission peaks result from emission of individual atoms, thereby creating spectra conducive to simplifying the identification of the chemical composition of the gases under investigation. Such accurate identification of components of the gas may allow for the precise determination of the stage of the process being performed, and in particular for detection of process endpoint.

Some embodiments of the present invention detect endpoint of a process of etching a silicon-containing dielectric layer, based upon changes in intensity of optical emissions characteristic of atomic silicon. According to certain embodiments, the optical emissions are taken directly from a plasma being utilized to perform the desired etching process. In other embodiments, the optical emissions are taken from gas sampled from the etching process. In these embodiments, a sufficient density of power is delivered to the sampled gas to dissociate large numbers of the molecules and molecular fragments into individual atoms. This creates spectra in which a change in intensity of emission peaks characteristic of atomic silicon, can readily be detected. In general, a decline in the intensity of emissions of atomic silicon is indicative of endpoint of a process for etching a silicon-containing dielectric.

Various additional objects, features and advantages of embodiments in accordance with the present invention can be more fully appreciated with reference to the detailed description and accompanying drawings that follow.

BRIEF DESCRIPTION OF THE DRAWINGS

FIG. 3 is a detailed view of the embodiment of the detection apparatus shown in FIG. 2.

FIG. 4 is shows a diagram of an embodiment of a match circuit for use with the detection apparatus of FIG. 3.

FIG. 11 shows a detailed chart of wavelengths, and relative intensities, characteristic of the emission of atomic silicon.

DETAILED DESCRIPTION

Certain embodiments of the present invention are directed to the analysis of the composition of a gas or gas mixtures under vacuum conditions. According to particular embodiments, techniques for the manufacture of semiconductor devices are provided. More specifically, embodiments of the present invention may use a spectrometer in conjunction with a self-contained plasma chamber to measure intensity and wavelength of light emitted from the plasma chamber, as the plasma excites the atoms and/or molecules comprising the gas being measured.

Embodiments of the present invention may be applied to the manufacture of advanced integrated circuits such as dynamic random access memory devices, static random access memory devices (SRAM), application specific integrated circuit devices (ASIC), microprocessors and microcontrollers, Flash memory devices, flat panel displays, MEMS, and others.

Embodiments of the present invention relate to methods and apparatuses for creating spectra conducive to identifying the chemical compositions of gases under investigation. These spectra may be created by providing sufficient power in the plasma to dissociate a large number of the molecules and molecular fragments into individual atoms. This approach is based on the recognition that the power delivered into the plasma does more than determine the intensity of emission from the plasma. Specifically, once the power density applied to the plasma reaches a sufficiently high level, the nature of the plasma emission spectrum changes. With sufficient power delivered into the plasma according to embodiments of the present invention, most of the emission peaks will result from emission of individual atoms rather than of molecules or molecular fragments.

Figure 2:
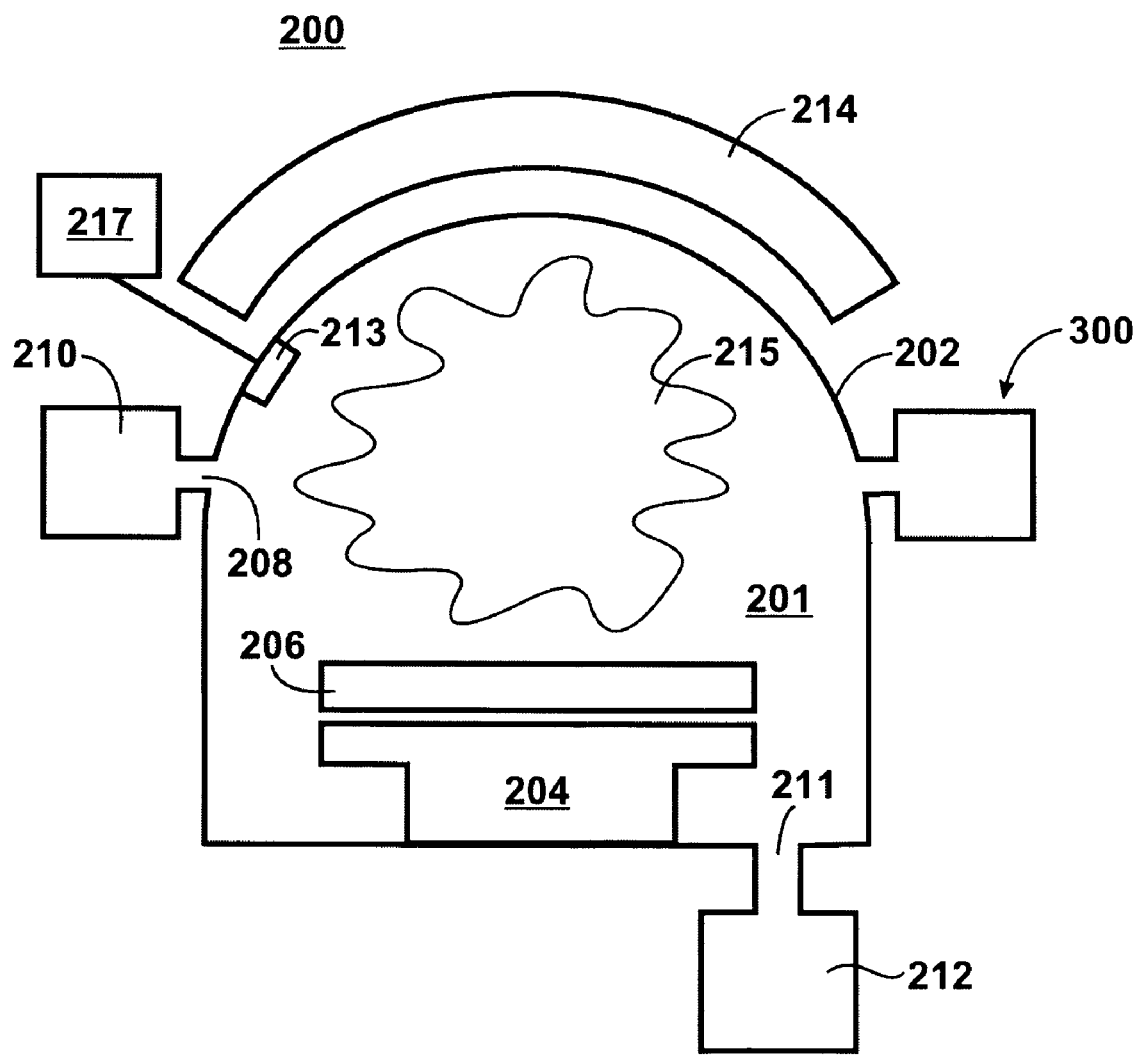
FIG. 2 shows a simplified schematic view of an embodiment of a plasma processing system utilizing an embodiment of a detection apparatus in accordance with the present invention.

FIG. 2 is a simplified view of an embodiment of an apparatus in accordance with the present invention for processing silicon wafers. Apparatus 200 includes a processing chamber 201 having walls 202 enclosing a chuck 204 configured to support a substrate 206. Chamber 201 includes an inlet 208 for receiving gas from a gas supply 210. Chamber 201 also includes an outlet 211 in connection with a vacuum pump 212.

Upon the loading of substrate 206 onto chuck 204, vacuum pump 212 is activated and evacuates chamber 201. Gas from gas supply 210 is flowed into the chamber, and an RF potential is applied from RF source 214 to the chamber to generate a plasma 215 therein. Application of a bias to the chuck 204 can result in reactive species in the plasma being attracted to the substrate to strike and etch material present thereon.

The state of the etching process occurring in the chamber of FIG. 2, can be discerned by monitoring the composition of the gas in the plasma chamber. In particular, emissions from the plasma can reveal the constituents thereof Thus, FIG. 2 also shows a plasma monitoring apparatus 300 in accordance with an embodiment of the present invention, in fluid communication with chamber 201. FIG. 3 shows an enlarged view of the plasma monitoring apparatus 300.

Basic components of an embodiment of the apparatus of FIG. 3 in accordance with the present invention, includes, an enclosure 301, plasma chamber 302 (where the molecules, molecular fragments, and atoms comprising the sampled gas are subjected to a plasma that dissociates enough of the multi-atom particles to create significant emission from individual atoms); a flange 303 connecting the chamber to a gas source, a RF (radio frequency) generator 304 that provides sufficient power into the plasma; and a spectrometer 308 that creates a spectrum from the plasma emission.

The apparatus of FIG. 3 also includes a pulse generator 306 to pulse the RF generator 304. In particular, certain embodiments of the present invention relate to methods and apparatuses that allow the high-powered plasma chamber to be compact and convenient for use, without requiring, for example, water cooling. Specifically, since monitoring of the chemical composition of a gas may be performed only at certain intervals (such as several times per second), power can be applied in a pulsed manner to generate the high energy plasma for only brief periods of time. If the percentage of time that the plasma is ignited is small, then the average power applied to the plasma chamber can be kept low, maintaining relatively low the heat delivered into the plasma chamber.

Figure 12:
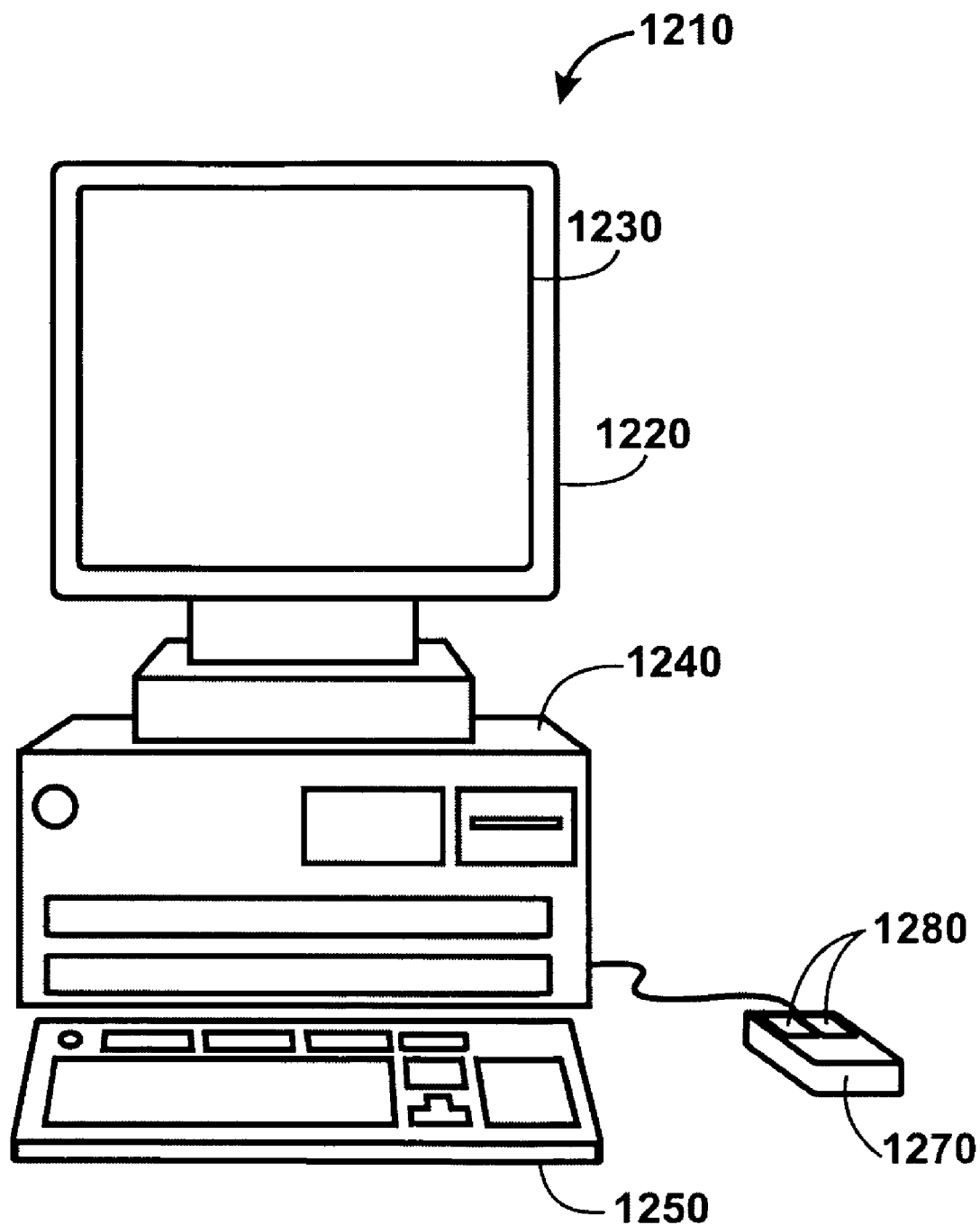
FIG. 12 is a schematic illustration of a computer system for use in accordance with embodiments of the present invention.
Figure 12A:
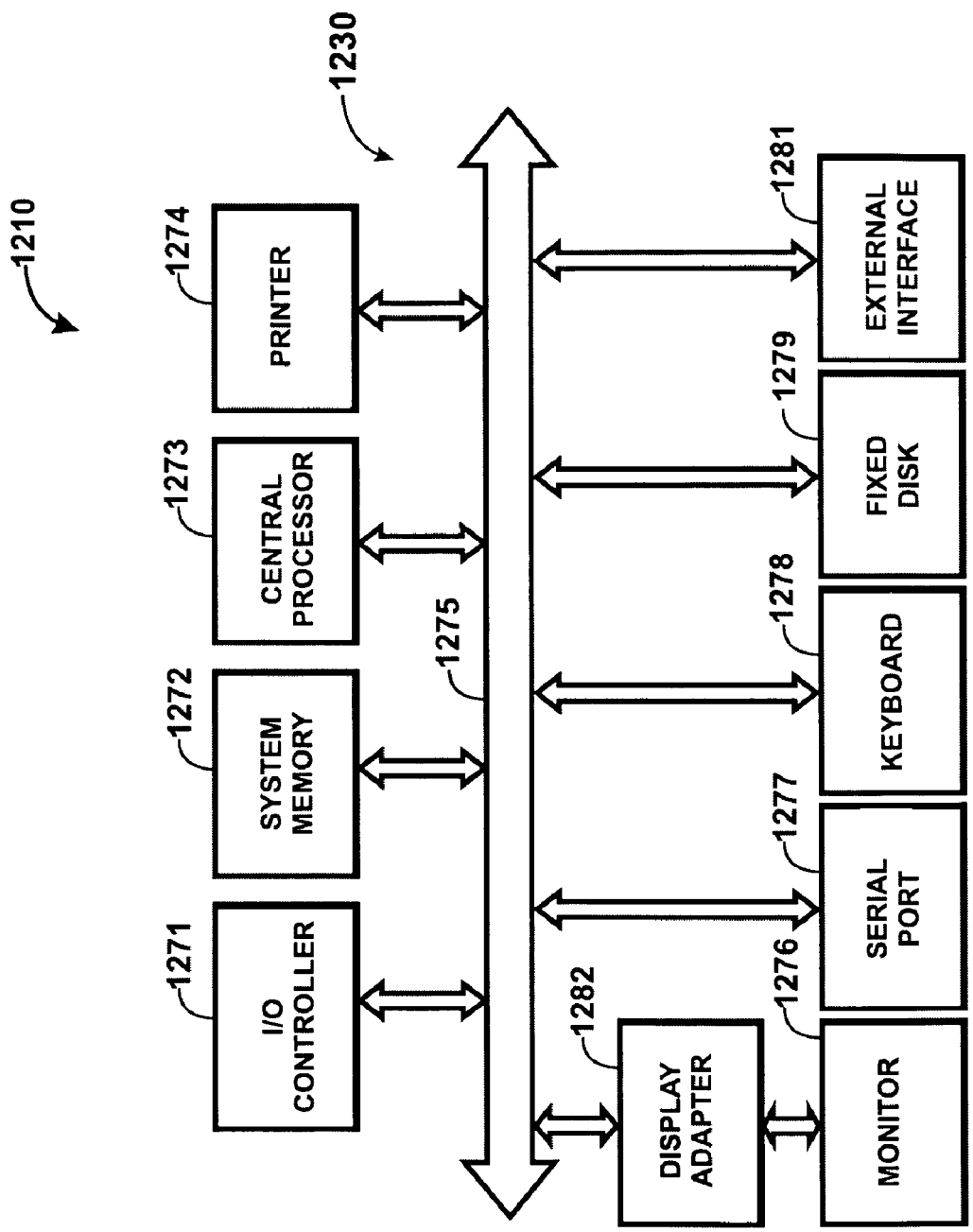
FIG. 12A is an illustration of basic subsystems the computer system of FIG. 12.

The apparatus of FIG. 3 further includes a computer or processor 310 to run the spectrometer. In particular, the computer or processor is configured to correlate intensity of emissions with relative concentrations of gases in the mixture. The computer/processor may also be configured to determine a stage of a process (such as endpoint) from the gas sample, based upon the relative concentrations of atoms in the gas or gas mixture. Specifically, the computer 310 may be in electronic communication with a computer-readable storage medium having stored thereon code configured to direct the computer to perform a variety of tasks relating to detection of gas composition and process control. FIGS. 12-12A below present additional detail regarding a computer system suitable for implementing embodiments in accordance with the present invention.

Chamber 302 is comprised of materials that can reliably withstand a high density plasma comprising reactive elements such as fluorine and other halogens, metallic ions, and oxygen ions, while at the same time not contributing any harmful contamination to the process being monitored. In accordance with one embodiment, materials exposed to the plasma include a high-purity $Al_2O_3$ tube 302, stainless steel endpieces 307a and 307b, and a high purity $Al_2O_3$ (sapphire) window 316 in endpiece 307b through which the emission from the plasma can be detected by the spectrometer 308.

Although the plasma in the chamber can be generated with a number of different electrode configurations, one of the simplest and most effective is an inductive winding 318 around the $Al_2O_3$ tube 302. In such an embodiment, the wire comprising this winding should be of sufficient gauge to carry the large currents required for the high power plasmas. For example, in the specific embodiment of FIG. 3, the winding is made from 12 American Wire Gauge (AWG) magnet wire.

The embodiment of FIG. 3 also shows the presence of a match network 320. Although many types of match networks could be used, one possible match network 320 is shown in the circuit 400 of FIG. 4. The primary consideration in the choice of components of the match network is to make sure that the components can withstand the voltages and currents associated with the high power delivered by the RF generator 304. The specific capacitors that were used in the embodiment of FIG. 4 were multilayer ceramic capacitors having a voltage rating of at least 5000 V obtained from American Technical Ceramics of Huntington Station, N.Y.

Many different types of RF generators could be used in accordance with embodiments of the present invention. Examples of suppliers of such suitable RF generators include companies such as Advanced Energy Industries, Inc. of Fort Collins, Co., MKS Instruments, Inc. of Wilmington, Mass., and others. The RF generator utilized in the specific embodiment of FIG. 3 was a Seren R601 available from Seren IPS, Inc. of Vineland, N.J., which allows a pulsed mode of operation.

Likewise, any one of a number of different spectrometers could be used to implement embodiments in accordance with the present invention. In the particular embodiment of FIG. 3, an HR4000 spectrometer available from Ocean Optics, Inc. of Dunedin, Fla., was utilized.

The collimating lens 322 of the embodiment of FIG. 3 is used to make sure that the emission from only a well defined part of the plasma, near the axis X of the plasma chamber, is measured. Typically the part of the plasma that is measured represents only a few percent of the total plasma.

The pulse circuit can be implemented in any number of different ways. One of the simplest and most compact approaches uses a small set of integrated circuits, including one or more monostable multivibrators. In the current embodiment, a 74LS123 dual monostable multivibrator is used.

Figure 5:
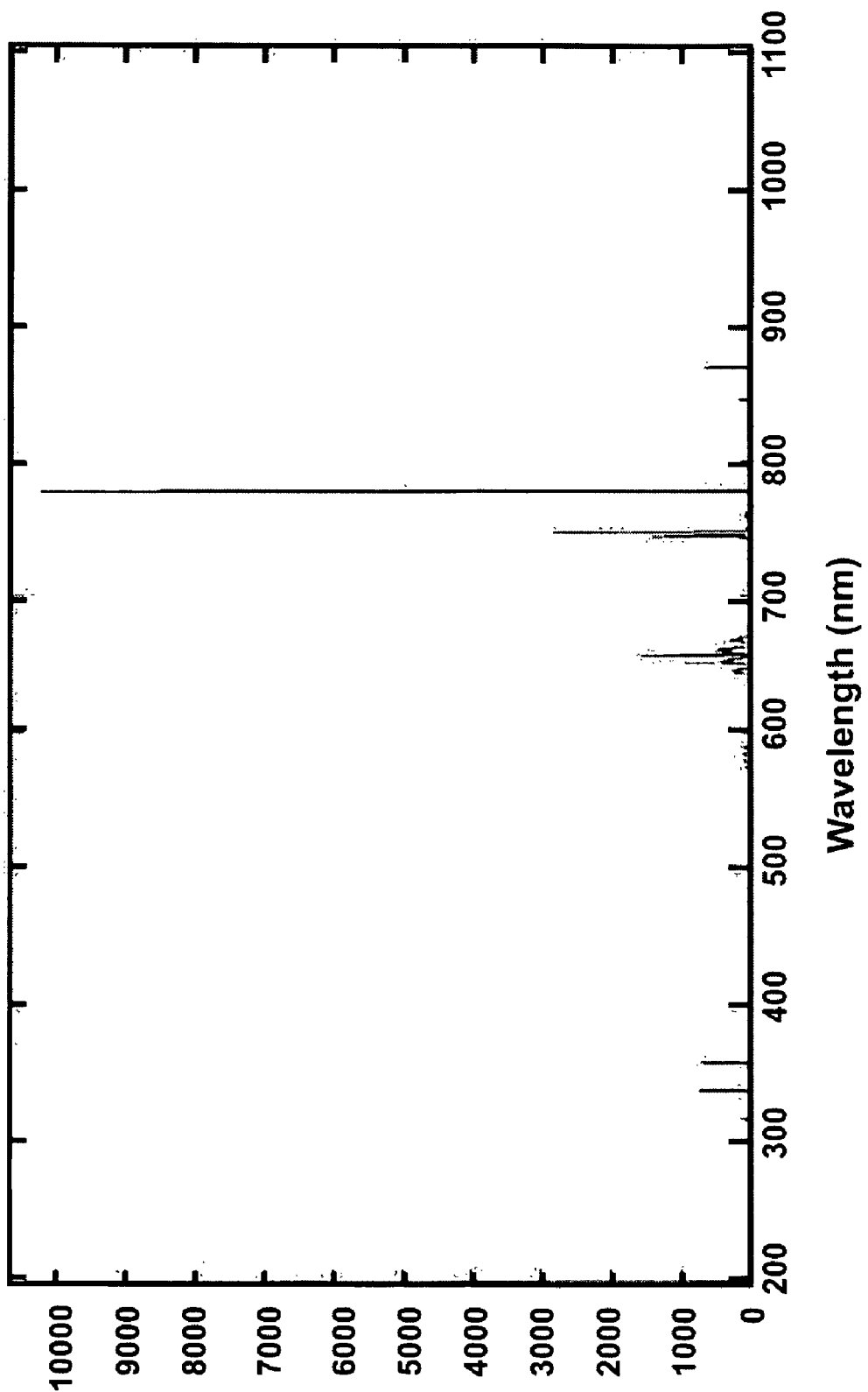
FIG. 5 is an emission spectrum of air produced by an embodiment of the present invention, with a high power delivered into the plasma.

In particular embodiments, pulsing can also be accomplished with the use of a microcontroller which communicates with the spectrometer and the generator, synchronizing the pulsing of the generator with the integration cycles of the spectrometer. The use of a microcontroller allows for flexibility of programming, the ability to upgrade easily, and the ability to accomplish these tasks remotely FIG. 5 shows a plasma emission spectrum from air obtained utilizing the embodiment of the present invention shown in FIGS. 2-4. The spectrum of FIG. 5 was obtained by applying RF energy to the chamber at a power of 500 Watts. Considering the volume of the plasma, this equates to a power density of approximately 20 Watts/cm$^3$.

Figure 1:
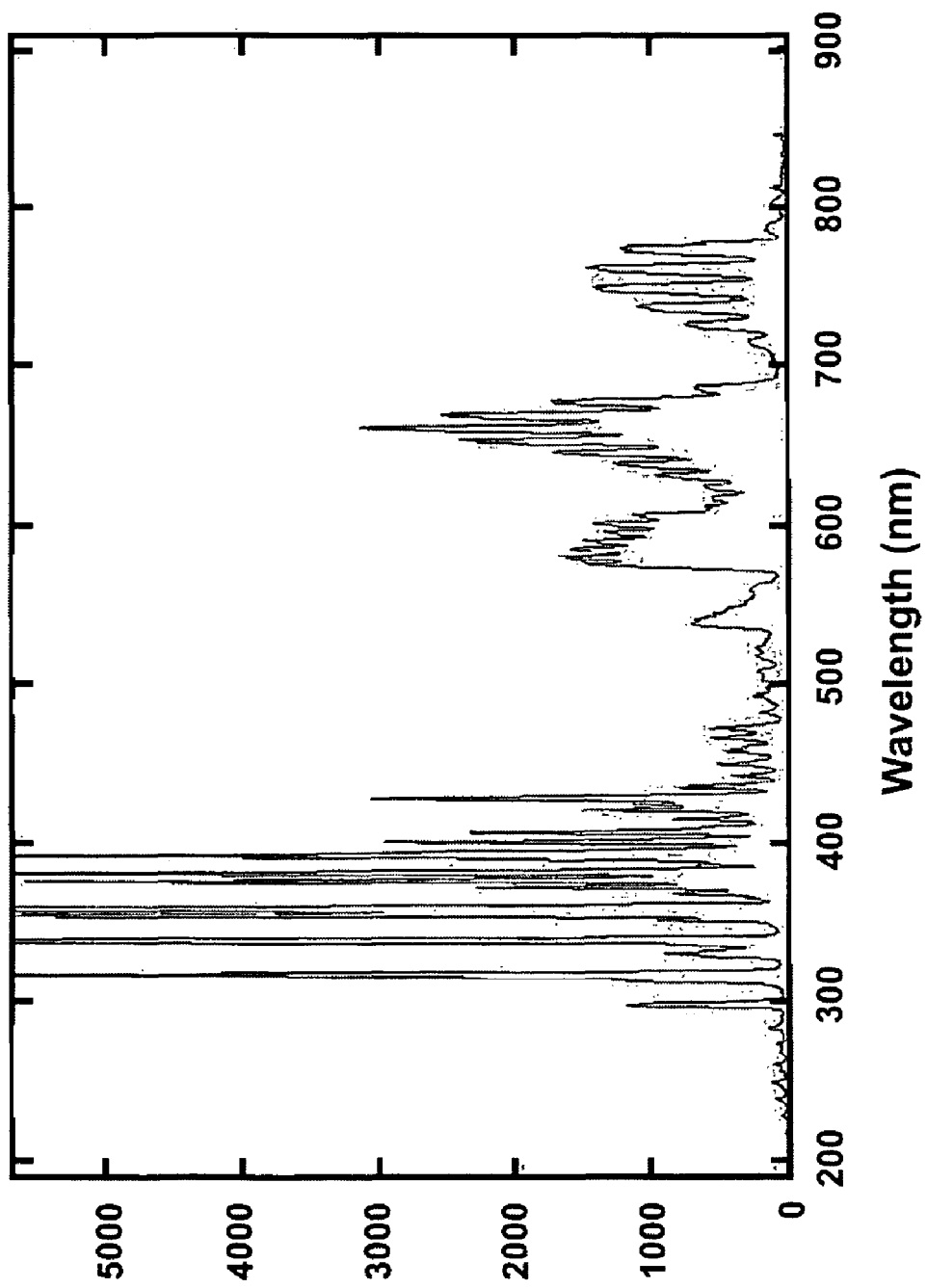
FIG. 1 shows a conventional emission spectrum of air.

By way of comparison, the conventional emission spectrum shown in FIG. 1 was obtained by applying RF energy of 4 Watts to a cylindrical chamber having a length of 1.8 cm and a diameter of 1.5 cm and thus containing a plasma having a volume of about 3.2 cm$^3$. This equates to a power density of approximately only about 1.3 Watts/cm$^3$.

According to embodiments of the present invention, the application of high RF power to the plasma results in the dissociation of molecules and molecular fragments into individual atoms, producing a much simpler spectrum. For example, the peaks of FIG. 5 occupy only a fraction of the entire spectrum, as they are few in number and sharp and narrow in a manner characteristic of atomic emission spectra. Contributions to the spectrum of FIG. 5 from molecules are hardly noticeable, where the only indication of molecular emission is the presence of several very small peaks in the mid-600 nm range and, even smaller yet, in the mid-700 nm range, and a couple peaks in the mid-300 nm range.

The emission spectrum of FIG. 5 conveys significantly more information than the conventional spectrum of FIG. 1. In particular, the sharp peaks at 742 nm, 744 nm, 747 nm, and 868 nm indicate emission from atomic nitrogen. The peaks at 777 nm and 845 nm indicate emission from atomic oxygen. The peak at 656 nm is likely atomic hydrogen from the small amount of moisture in the air.

Figure 6:
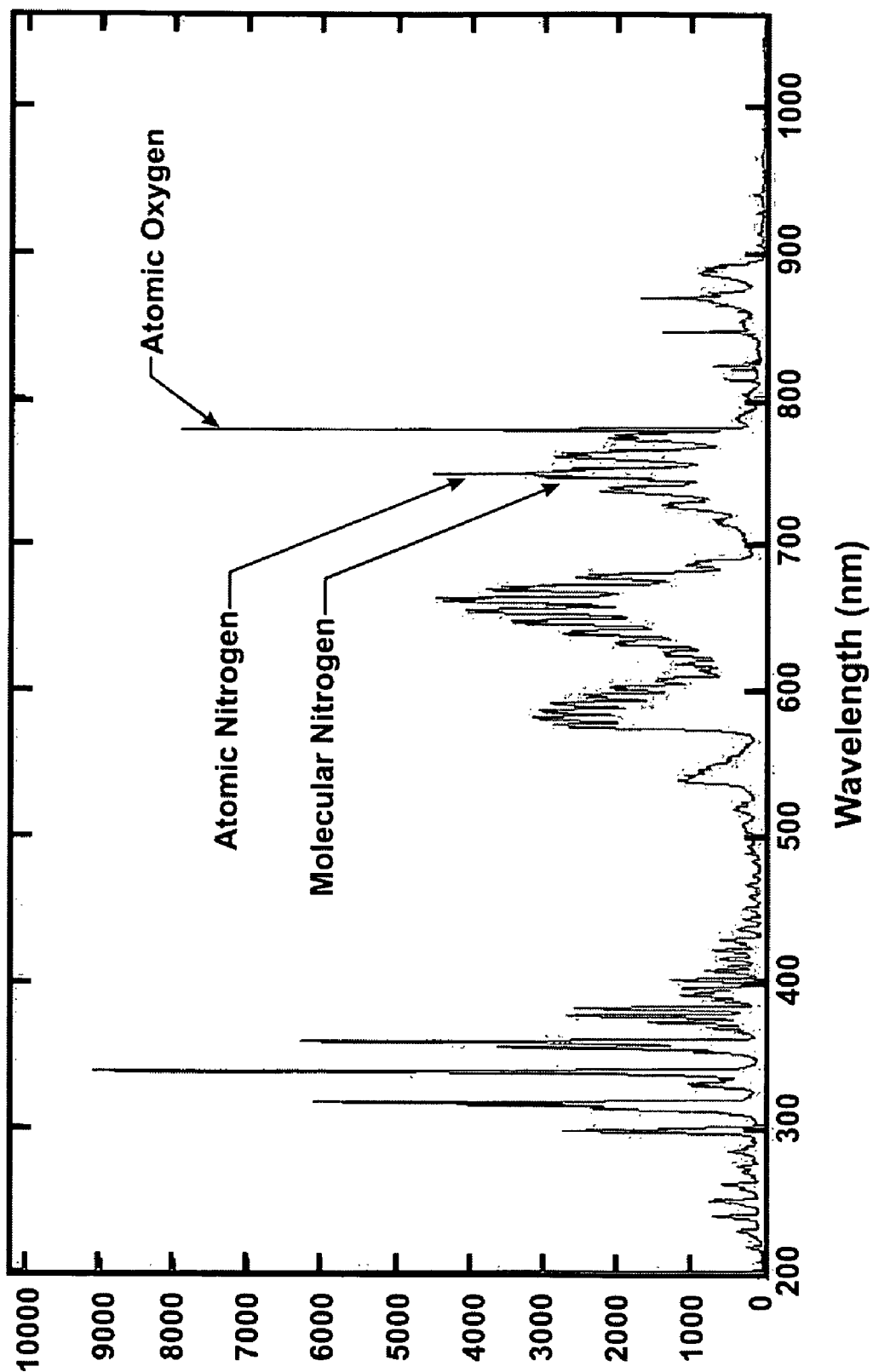
FIG. 6 is an emission spectrum of air produced by an embodiment of the present invention, with a lesser power delivered into the plasma.

FIG. 6 shows a spectrum of a plasma containing air resulting from an embodiment of a detection apparatus in accordance with the present invention, operated at a lower power level. Specifically, in this case the power delivered by the RF generator to the plasma was 180 Watts, corresponding to a power density of about 7.2 Watts/cm$^3$. In the spectrum of FIG. 6, emission from molecular nitrogen as well as from atomic nitrogen and atomic oxygen can be seen.

Peaks for atomic nitrogen at 747 nm, and for atomic oxygen at 777 nm, are indicated in the FIG. 6. Underneath these peaks is a region produced by molecular nitrogen, which has a number of broad peaks extending from about 700 nm to about 800 nm. Comparison of this portion of the spectrum with the corresponding portion in FIG. 1 (for a lower power case), indicates that the spectra look very similar except for the presence of the isolated, narrow peaks for atomic nitrogen and atomic oxygen. Thus, the spectrum in FIG. 6 can be considered as the superposition of the molecular emission (where the shape of the spectrum is very similar to the shape of the spectrum in FIG. 1) and the atomic emission, with the narrow peaks at 747 and 777 nm.

In summary, three general types of spectra with regard to the emission from atoms as compared to the emission from molecules and molecular fragments, can be identified. A low power spectrum, for example as shown in FIG. 1, is produced in the low-power region where the emission is primarily from molecules and molecular fragments and no significant signals from atoms can be seen. A high-power spectrum, for example as shown in FIG. 5, is produced in the high-power region where the emission is primarily from atoms. A medium-power spectrum, for example as shown in FIG. 6, is produced in a transition region where there is still emission from molecules and molecular fragments, but the emission from atoms is significant.

For some applications, an emission spectrum having the signal strength of atomic emission shown in FIG. 6 could be sufficient. In other cases, it may be necessary for the atomic emission to be much greater than the molecular emission, for example as shown in FIG. 5. Depending on the particular requirements of the system, the optimum power level can be chosen.

Embodiments in accordance with the present invention may apply sufficient RF power to the plasma such that significant fraction of optical emissions from the plasma are from individual atoms. For example, in accordance with one embodiment of the present invention, the power provided to the plasma may be such that an intensity of emission from atomic nitrogen in air at 747 nm, is at least 20% of an intensity of emission from molecular nitrogen at 747 nm.

Quantitative estimates of the relative contributions of molecular and atomic lines at a wavelength of interest (for example 747 nm), can be obtained by examining the strength of the molecular band in a band surrounding the wavelength of interest. For example, regarding the 747 nm region in FIGS. 1 and 6, we can see that the spectrum of FIG. 6 is a superposition of a molecular spectrum whose shape can be obtained from an analysis of FIG. 1, and an additional narrow peak at 747 nm corresponding to atomic nitrogen emission. Fitting the shape of the molecular band could comprise a superposition of a collection of Gaussian peaks whose centers, widths, and heights, were determined by fitting to the low power spectrum of FIG. 1. These would be scaled by an overall constant to give the best fit to the molecular band in the neighborhood of 747 nm in the spectrum shown in FIG. 6. This would provide an estimate for the molecular contribution at 747 nm, with the balance of the observed intensity being due to atomic emission. A similar approach could be used elsewhere in the spectrum to quantitatively estimate the separate contributions of molecular and atomic emissions.

In accordance with another embodiment, the power provided to the plasma may be such that an intensity of emission from atomic carbon at 248 nm is at least 20% of an intensity of the emission from molecular CO at 520 nm for a plasma etching process where silicon oxide is being etched in a fluorocarbon/oxygen chemistry. In accordance with still another embodiment, the power provided to the plasma may be such that an intensity of emission from atomic silicon at 251 nm is at least 20% of an intensity of emission from molecular SiF at 440 nm for a plasma etching process where silicon oxide is being etched in a fluorocarbon/oxygen chemistry. In accordance with yet another embodiment, the power provided to the plasma may be such that an intensity of emission from atomic F at 686 nm is at least 20% of an intensity of emission from molecular CO at 520 nm in a fluorocarbon/oxygen chemistry.

Embodiments of the present invention may apply sufficient RF power to achieve a power density of between about 3-40 W/cm$^3$, depending upon the particular components of the plasma. Depending upon the particular embodiment, examples of apparatuses in accordance with the present invention may be configured to apply RF power to achieve a power density greater than about 3 W/cm$^3$, a power density greater than about 5 W/cm$^3$, a power density greater than about 10 W/cm$^3$, a power density greater than about 15 W/cm$^3$, a power density greater than about 20 W/cm$^3$, a power density greater than about 25 W/cm$^3$, a power density greater than about 30 W/cm$^3$, a power density greater than about 35 W/cm$^3$, or a power density greater than about 40 W/cm$^3$.

Certain gases exist in atomic form, regardless of whether a plasma is present or not. Inert gases such as argon and neon, behave this way. However, from a practical point of view, many of the measurements desired to be taken by embodiments according to the present invention, will be of mixtures containing gases that in the absence of a plasma or in a low-powered plasma, will not be present in atomic form.

One example of an application for embodiments in accordance with the present invention is monitoring of plasma cleaning processes commonly employed to remove contamination from plasma chambers. Specifically, the purpose of a dry clean is to remove the build-up of plasma etch products that occurs during the etching of silicon wafers used in semiconductor device manufacturing. During a dry clean, oxygen gas is typically introduced into the plasma etch chamber, and a plasma is ignited. The oxygen combines with the built-up deposits on the chamber walls, forming volatile compounds that are then pumped out of the chamber.

Figure 7:
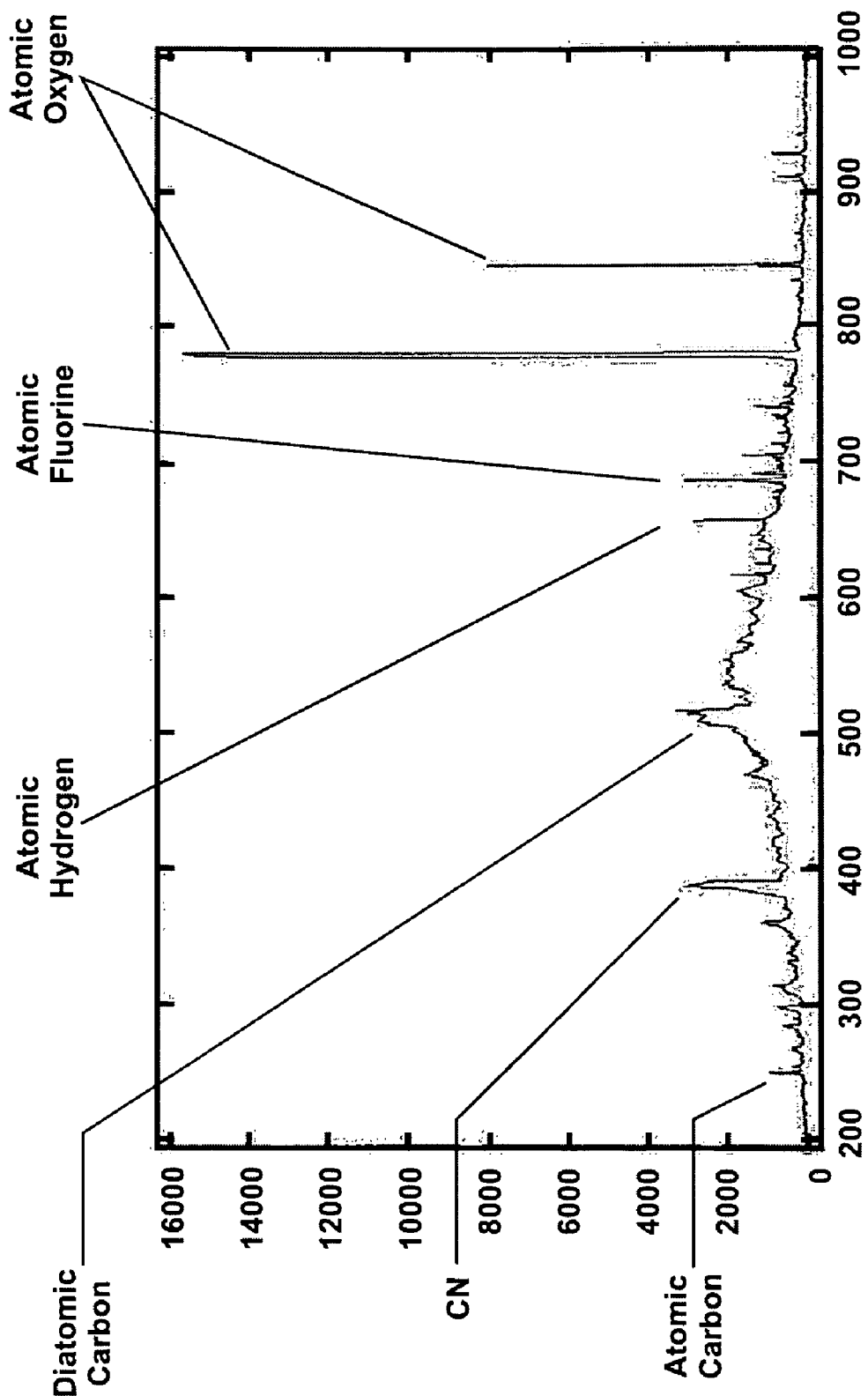
FIG. 7 is an emission spectrum of a plasma chamber cleaning process produced by an embodiment of the present invention.

FIG. 7 shows an emission spectrum produced by an embodiment of the present invention, from a gas mixture inside a plasma etch chamber during such a "dry clean" process. In FIG. 7, the presence of the oxygen is clearly seen, along with carbon, fluorine, and hydrogen that are the primary constituents of the build-up on the chamber walls. There is also a small amount of nitrogen present, typically from atmospheric contamination. This nitrogen combines with carbon, forming a very strong bond that survives even the plasma power levels typically used in the present invention. By monitoring the peaks associated with these various atoms, significant understanding about the behavior of the dry clean can be gained. For example, the intensity of the carbon peak can provide a good measure of the progress of the dry clean as the carbon deposits are removed from the chamber.

Figure 8:
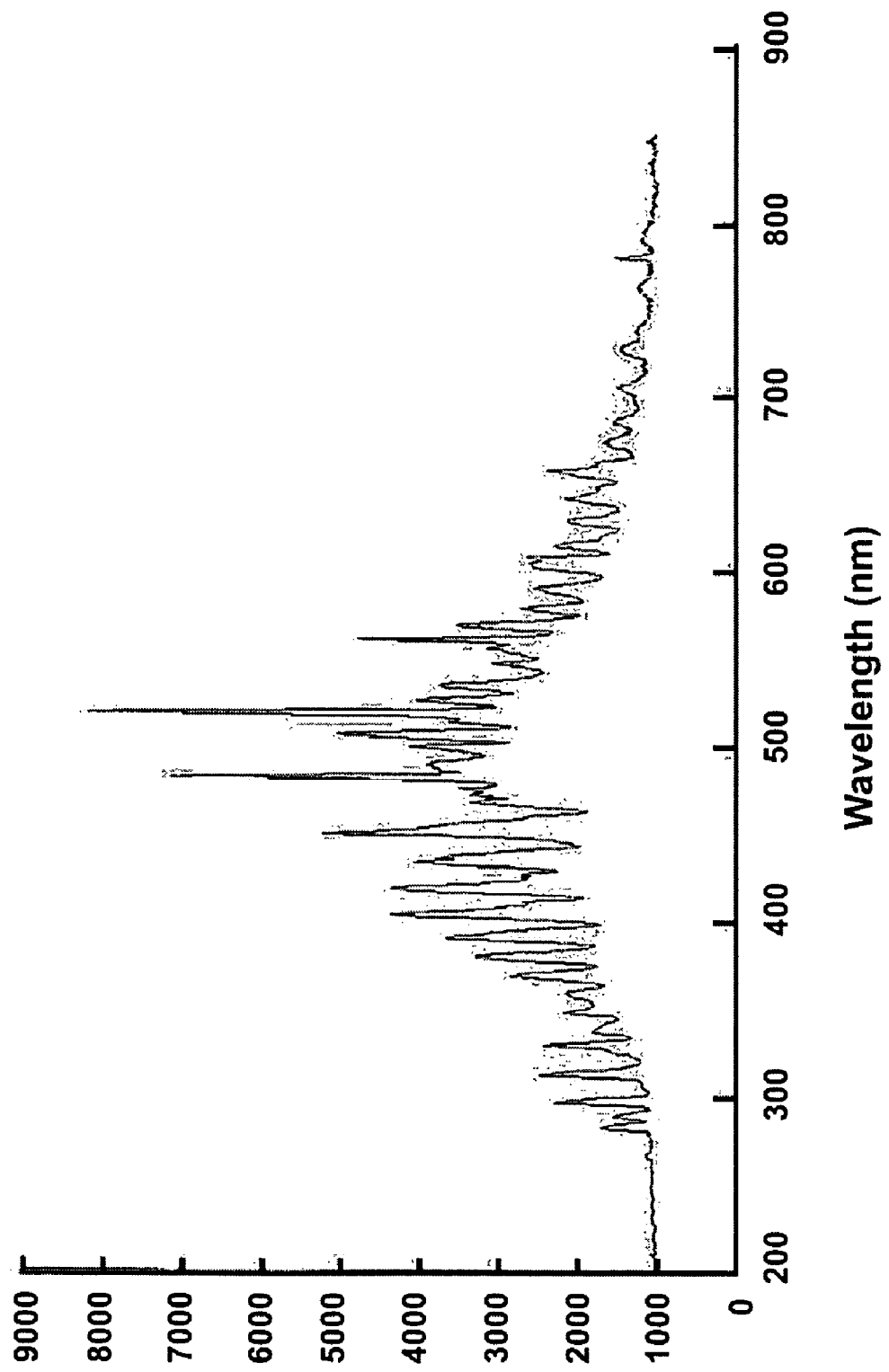
FIG. 8 is a conventional emission spectrum of a plasma chamber cleaning process.

FIG. 8 shows a conventional emission spectrum of such a dry clean process, obtained at a power density of only about 1.3 W/cm$^3$. FIG. 8 shows no clear indication of the presence of oxygen, notwithstanding the fact that oxygen comprises the major fraction of plasma. In addition, the readily identifiable peaks indicative of atomic carbon, fluorine, and hydrogen, are also not able to be discerned from this spectrum.

The spectrum of FIG. 8 does contain a large number of peaks and bands, most of which are attributable to the presence of molecules and molecular fragments. For example, some of the peaks are indicative of CO; other peaks might be indicative of larger molecules or molecular fragments that contain various amounts of carbon, fluorine, oxygen, and/or hydrogen. Trying to track these elements across the myriad molecules and molecular fragments is an extremely difficult task, made even more difficult by the fact that some of the peaks might not have any known identification.

Figure 9:
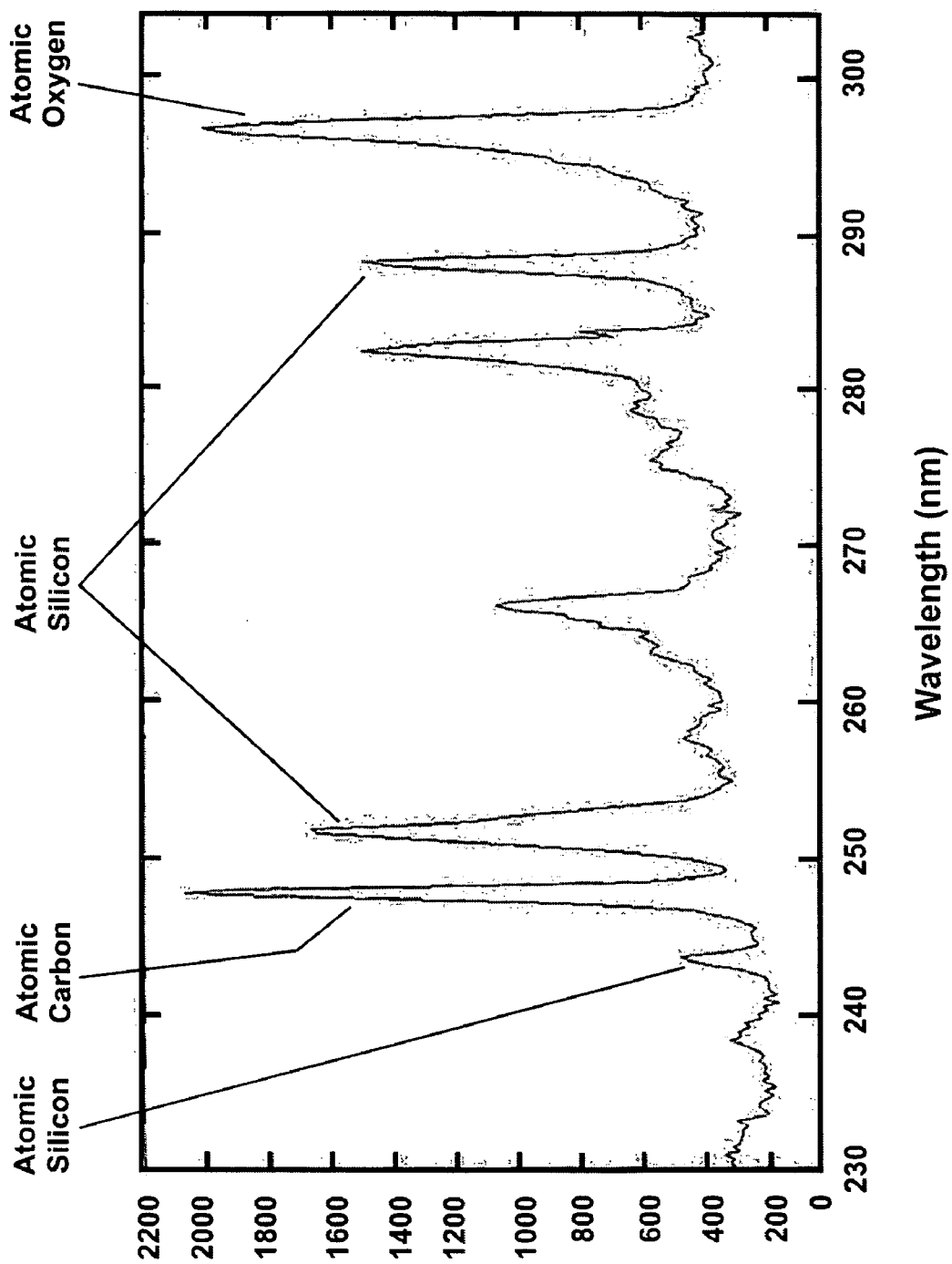
FIG. 9 is an emission spectrum of a plasma etching process produced by an embodiment of the present invention.

Another possible application for embodiments in accordance with the present invention is to monitor progress of a process of actually etching a material on a semiconductor substrate utilizing a plasma. FIG. 9 shows a spectrum produced by an embodiment of the present invention of a gas mixture inside of a plasma etch chamber during the etching of a silicon oxide film on a silicon wafer. The etching of FIG. 9 is taking place utilizing a fluorocarbon/oxygen chemistry comprising 10 sccm (standard cubic centimeters per minute) of $C_4F_8$, 50 sccm of CO, 5 sccm of $O_2$, and 200 sccm of Ar. Part of the oxide film is protected by a photoresist layer patterned such that the protected oxide will be present in exactly the right locations to form part of an interconnect scheme of a particular semiconductor device.

FIG. 9 shows the peaks associated with carbon, which is coming from the photoresist as well as the gas mixture entering the plasma chamber; oxygen, which is coming from the silicon oxide as well as the gas mixture entering the plasma chamber; and silicon, which is coming from the silicon oxide that is being etched. Monitoring of these peaks can convey significant amounts of information on the progress of the plasma etching process. For example, the intensity of the silicon peak can reveal the rate of oxide etching, providing an indication of change in the etch rate, as well as indicating when the etching process is completed (endpoint).

Figure 10:
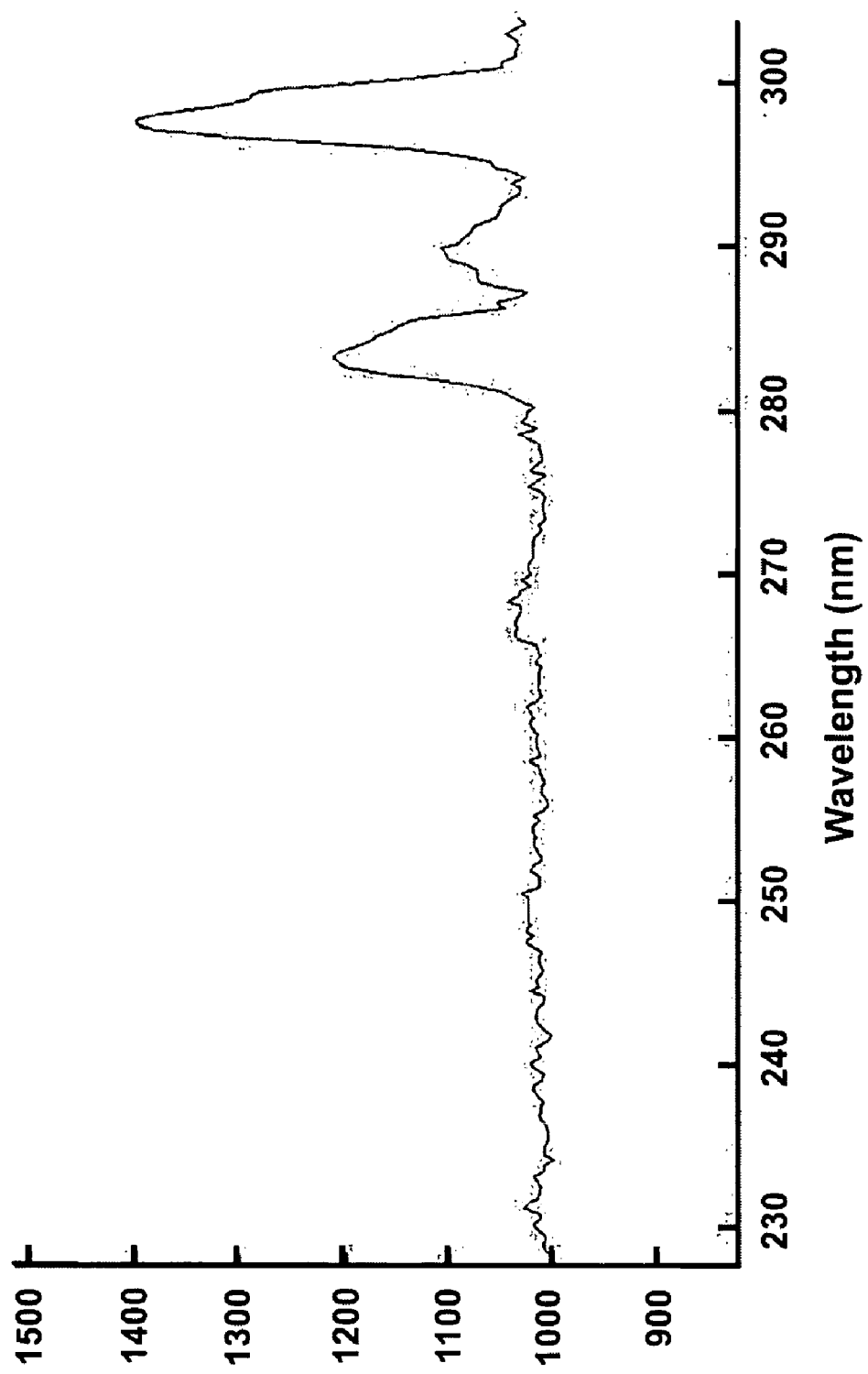
FIG. 10 is a conventional emission spectrum of a plasma etching process.

By contrast, FIG. 10 shows a conventional emission spectrum of the same gas mixture of FIG. 9, obtained at low power. To be noted in FIG. 10 is the complete absence of any peaks associated with silicon or carbon. These elements are contained in molecules or molecular fragments that are producing emission peaks or bands at other wavelengths. However, identifying the presence of these elements from these other peaks is an extremely difficult task.

A desirable characteristic of a gas monitoring system is that the plasma chamber be compact and portable. Ideally, it should not require water cooling. If the high power levels of the present invention were delivered continuously, water cooling would most likely be necessary. In most cases, however, measurement of the gas composition only needs to occur at specific intervals, such as once per second, or perhaps several times per second, or in some cases, significantly less often. Since power levels of hundreds of Watts can create a high level of emission and since most spectrometers are quite sensitive, a high quality spectrum can be obtained in the present invention within several milliseconds. Consequently, another component of the present invention is to pulse the RF generator, i.e., turn it on, for a period of milliseconds every time that a gas measurement is desired, which can be only several times per second or less. Under these circumstances, the average power delivered into the plasma chamber is on the order of 1% of the maximum power delivered.

In one example, the emission spectrum shown in FIG. 5 was obtained utilizing a pulsed application of RF energy. In particular, the RF energy was applied in the form of a 2 millisecond pulse that occurred 5 times per second. With a maximum power level of 500 Watts, this results in an average power level of 5 Watts. For the emission spectrum shown in FIG. 7, the maximum power was 300 Watts (corresponding to a power density of 12 Watts/cm$^3$), the pulse duration was 3 milliseconds, and the pulse frequency was 5 times per second, resulting in an average power level of 4.5 Watts. For the emission spectrum of FIG. 9, the maximum power was 300 Watts (corresponding to a power density of 12 Watts/cm$^3$), the pulse duration was 12 milliseconds, and the pulse frequency was 5 times per second, resulting in an average power level of 18 Watts.

Utilization of a pulsed application of RF power in accordance with embodiments of the present invention, may confer certain benefits. One such benefit of a low average power level, is avoidance of the need for any external cooling of the apparatus, for example by circulation of cooling water requiring a cold water source and special fluid handling connections. Indeed, in many instances, a simpler type of cooling device such as a fan, or even no cooling device at all, need be employed.

Embodiments in accordance with the present invention can, but need not, apply power in a pulsed manner. In various embodiments, power can be applied in pulses having a duration of between about 0.5 milliseconds to 50 milliseconds. In certain embodiments, the pulse can occur with a frequency of about once per second to about 20 times per second. In some cases, the process may be changing so slowly that a pulse every minute or even less would be sufficient. Depending upon the duration and frequency of the pulsed energy, the average power in the plasma can be between about 0.1 to about 50 W.

Various embodiments according to the present invention may provide certain advantages such as a clear end point signal indicated by a robust, distinguishable, recognizable and consistent End Point Index (EPI) signal. Ease of use may be indicated by simple set-up, no complex algorithm to develop, and no special user training required. Other potential advantages offered by particular embodiments in accordance with the present invention may include versatility and therefore ideally suited for multiple dielectric etch processes across different exposed areas, nodes and film substrates with little to no configuration changes. Of course there can be many variations, modification, and alternatives.

Advantages offered by approaches according to various embodiments of the present invention can include the following:
1. Emission peaks for individual atoms have been well documented.
2. Emission peaks for individual atoms are typically narrower than for molecules and molecular fragments, which typically emit in bands, and there are typically fewer peaks, thus preventing significant overlap of peaks from different atoms and making identification of the specific constituents of the gas much easier.
3. Tracking the behavior of a particular element becomes easier, since there are not an unknown number of molecules or molecular fragments that might contain that particular element.
4. For those applications where a plasma process is being monitored, the spectrum is much less sensitive to any variations or fluctuations of the main plasma since the particular molecules and/or molecular fragments formed by the main plasma are broken apart into atoms prior to emission.

Certain benefits can be achieved according to embodiments of the present invention. For example, various embodiments of the present invention provide one end point solution for multiple processes, technology nodes, exposed areas, and film types. Embodiments in accordance with the present invention may provide an effective tool excursion and outlier control resulting in increased tool throughput. Embodiments of the present invention may also provide chamber matching of end point performance, as well as extension of current capital equipment to future technology nodes. Certain embodiments of the present invention may provide a way to process devices in a plasma ambient, which can result in a more efficient process and a better controlled process. One or more embodiments in accordance with the present invention can be applied to a variety of applications such as memory, ASIC, microprocessor, flat panel display, MEMS, and other devices.

Although a number of specific embodiments are shown and described above, embodiments of the invention are not limited thereto. For example, while the example described above utilizes the application of energy in the form of radio frequency (RF) radiation to a chamber, the present invention is not limited to this particular embodiment. Alternative embodiments in accordance with the present invention can utilize the application of other forms of radiation to a chamber, including but not limited to microwaves. For purposes of this application we define RF energy to be electromagnetic radiation whose frequency lies within the range from 100 kHz to 10 GHz.

Moreover, it is understood that the present invention is not limited to sensing characteristics of a plasma-based process (etching or deposition process). Rather, the gaseous composition from any type of manufacturing process, including semiconductor manufacturing processes, can be analyzed according to embodiments of the present invention. For example, embodiments in accordance to the present invention can be applied to detect end point for a deposition process, including but not limited to plasma-enhanced chemical vapor deposition (PECVD), high density plasma chemical vapor deposition (HDP-CVD), and other forms of chemical vapor deposition, such as low pressure chemical vapor deposition (LP-CVD).

The present invention is not limited to detecting composition of gases at any specific pressure. However, some embodiments of the present invention may be particularly well-suited for detecting the composition of gases present at sub-atmospheric pressure. In certain embodiments, gas composition may be detected within a pressure range of between about 0.1 milliTorr and about 100 Torr. In certain embodiments, gas composition may be detected within a pressure range of between about 3 milliTorr and about 10 Torr. In certain embodiments, gas composition may be detected within a pressure range of between about 3 milliTorr and about 500 milliTorr.

Particular embodiments of the present invention detect endpoint of a process of etching a silicon-containing dielectric layer, based upon changes in intensity of optical emissions characteristic of atomic silicon. According to certain embodiments, the optical emissions are taken directly from a plasma being utilized to perform the desired etching process. In other embodiments, the optical emissions are taken from gas sampled from the etching process. In these embodiments, a sufficient density of power is delivered to the sampled gas to dissociate large numbers of the molecules and molecular fragments into individual atoms. This creates spectra in which a change in intensity of emission peaks characteristic of atomic silicon, can readily be detected. In general, a decline in the intensity of emissions of atomic silicon is indicative of endpoint of a process for etching a silicon-containing dielectric.

A primary component of silicon-containing dielectric films is silicon. Moreover, it is relatively rare for any silicon-containing gas to be introduced as part of the chemistry utilized for etching. Accordingly, monitoring of concentrations of silicon in an etching environment can provide a direct and accurate means for determining when endpoint of an etching process has been reached.

Embodiments of the present invention determine the endpoint of the etching of silicon-containing dielectric films by detecting a change in the optical emission signal of atomic silicon. The following Table 1 provides a listing of the wavelengths and relative intensities of peaks of optical emissions characteristic of atomic silicon:

TABLE 1

Silicon

| Observed Wavelength of Peak | Relative Intensity of Peak |
|---|---|
| 243.589 | 300 |
| 250.766 | 425 |
| 251.508 | 375 |
| 251.6870 | 500 |
| 251.9960 | 350 |
| 252.4867 | 425 |
| 252.9269 | 450 |
| 288.2424 | 1000 |
| 390.6629 | 300 |
| 729.1181 | 400 |
| 740.7814 | 375 |
| 742.5542 | 425 |

FIG. 11A is a more detailed chart setting forth a more comprehensive listing of wavelengths indicative of the emissions from the first ionization level of atomic silicon. This comprehensive listing was obtained on-line from the National Institute of Standards and Technology (NIST) at the following location: http://physics.nist.gov/asd3. National Institute of Standards and Technology, Gaithersburg, Md. Ralchenko, Yu., Jou, F.-C., Kelleher, D. E., Kramida, A. E., Musgrove, A., Reader, J., Wiese, W. L., and Olsen, K. (2007). NIST Atomic Spectra Database (version 3.1.3). According to embodiments of the present invention, changes in optical intensity of one or more of these wavelengths can be monitored during etching, in order to accurately detect endpoint of the process.

According to embodiments of the present invention, endpoint in a process of etching silicon dioxide dielectric material is indicated by a change in the intensity of one or more of the wavelengths for atomic silicon shown above. Most typically, endpoint in the etching process will be revealed by a decline in intensity of the peak indicative of atomic silicon, as the amount of the silicon-containing by products from the reaction of the etching chemistry with the dielectric, will drop as the dielectric material is exhausted. The size of the drop in the intensity of emission will depend on a variety of factors, including the amount of silicon containing oxide material being etched (etching of a large surface area will produce a relatively large amount of silicon, and hence a strong emission signal). Under certain circumstances, however, the endpoint of an etching process may result in an increased emission of atomic silicon. In general, embodiments in accordance with the present invention are configured to detect a change in intensity of a peak characteristic of atomic silicon of 0.1% or greater.

In accordance with certain embodiments, endpoint can be determined by monitoring intensity of emissions from other atomic species in addition to silicon. For example, where the silicon containing dielectric comprises silicon oxide, endpoint of the etching process can be determined by monitoring a changed intensity of an emission peak of atomic oxygen, in addition to monitoring one or more emission peaks of atomic silicon.

In certain embodiments, the plasma that is being used to etch the silicon-containing dielectric film has sufficient power to disassociate most of the molecules into their atomic constituents. In other embodiments, the silicon dioxide being etched may cover large areas of the substrate, resulting in a strong signature emission of atomic silicon. In such embodiments, a spectrometer may be positioned in direct optical communication with the processing chamber in order to measure the emission of atomic silicon directly from the main processing plasma. Where it is possible to use a processing plasma having sufficient power, the embodiments just described can simplify the endpoint detection apparatus considerably.

However, for most plasma etching processes, the power applied to the processing plasma is not sufficient to provide a sufficiently strong signal from the emission of atomic silicon in order to allow detection of endpoint. This is because the application of high power can damage the fragile structures being fabricated.

Accordingly, in alternative embodiments a changed optical emission of atomic silicon indicative of endpoint, may be detected by sampling gas from the chamber, and then exposing the sampled gas to sufficiently strong RF power to dissociate molecules from the sample into their constituent atoms.

In one embodiment, a sufficient power is applied from the RF generator (for example 100-500 Watts) to dissociate a large fraction of the molecules that contain silicon. Since a primary source of the silicon atoms is from the etching of the silicon-containing dielectric film, and since measurement of the silicon atoms makes their chemical reaction path (whether they were in the form of $SiF_4$ or $SiF_3$, etc. after being etched from the film) irrelevant, measurement of the intensity of atomic silicon allows for a direct and accurate measurement of the endpoint of the silicon oxide film etching.

Returning to the apparatus of FIG. 2, the state of the etching process occurring in the chamber of FIG. 2, can be discerned by monitoring the composition of the gas in the plasma chamber. In particular, emissions from the plasma can reveal the constituents thereof.

Under certain conditions, the state of the etching process occurring in the chamber of FIG. 2, can be monitored based upon direct emissions from the processing plasma. Accordingly, FIG. 2 shows an optical window 213 in the chamber in optical communication with a spectrometer 217 configured to detect intensity of emission in one or more of the wavelengths listed in Table 1 and in FIG. 11.

More commonly, however, the energy of the processing plasma present in the chamber is not sufficiently high to result in dissociation of most molecules and molecular fragments into their component atoms. Accordingly, FIG. 2 also shows a plasma monitoring apparatus 300 in accordance with an embodiment of the present invention, in fluid communication with chamber 201. FIG. 3 shows an enlarged view of the plasma monitoring apparatus 300.

Embodiments in accordance with the present invention may apply sufficient RF power to the plasma such that significant fraction of optical emissions from the plasma are from individual atoms. For example, in accordance with one embodiment of the present invention, the power provided to the plasma may be such that an intensity of emission from atomic silicon at 251 nm is at least 20% of an intensity of emission from molecular SiF at 440 nm, for a plasma etching process where silicon oxide is being etched in a fluorocarbon/oxygen chemistry.

One possible application for embodiments in accordance with the present invention is to monitor progress of a process of actually etching a material on a semiconductor substrate utilizing a plasma. FIG. 9 shows a spectrum produced by an embodiment of the present invention of a gas mixture inside of a plasma etch chamber during the etching of a silicon oxide film on a silicon wafer. The etching of FIG. 9 is taking place utilizing a fluorocarbon/oxygen chemistry comprising 10 sccm (standard cubic centimeters per minute) of $C_4F_8$, 50 sccm of CO, 5 sccm of $O_2$, and 200 sccm of Ar. Part of the oxide film is protected by a photoresist layer patterned such that the protected oxide will be present in exactly the right locations to form part of an interconnect scheme of a particular semiconductor device.

FIG. 9 shows the peaks associated with carbon, which is coming from the photoresist as well as the gas mixture entering the plasma chamber; oxygen, which is coming from the silicon oxide as well as the gas mixture entering the plasma chamber; and silicon, which is coming from the silicon oxide that is being etched. Monitoring of these peaks can convey significant amounts of information on the progress of the plasma etching process. For example, the intensity of the silicon peak can reveal the rate of oxide etching, providing an indication of change in the etch rate, as well as indicating when the etching process is completed (endpoint).

By contrast, FIG. 10 shows a conventional emission spectrum of the same gas mixture of FIG. 9, obtained at low power. To be noted in FIG. 10 is the absence of any discernable peaks associated with silicon or carbon. These elements are contained in molecules or molecular fragments that are producing emission peaks or bands at other wavelengths. However, identifying the presence of these elements from these other peaks is an extremely difficult task.

Embodiments of the present invention may be applied to the manufacture of advanced integrated circuits such as dynamic random access memory devices, static random access memory devices (SRAM), application specific integrated circuit devices (ASIC), microprocessors and microcontrollers, Flash memory devices, flat panel displays, MEMS, and others.

Embodiments in accordance with the present invention are not limited to identifying only endpoints in processes. In accordance with alternative embodiments, etch rates can be determined, concentrations of various gases can be measured, and trace contamination, such as that from leaks into the process chamber, can be identified.

And while the above example describes endpoint detection based upon silicon content, the present invention is not limited to sensing this particular element. Alternative embodiments could detect emissions characteristic of other elements, and remain within the scope of the present invention. For example, Tables 2-12 below provide more comprehensive listings of emission spectra for carbon, oxygen, nitrogen, fluorine, hydrogen, phosphorus, iodine, chlorine, germanium, hafnium, and gallium, respectively.

TABLE 2

Carbon

| Observed Wavelength of Peak | Relative Intensity of Peak |
|---|---|
| 247.856 | 800 |
| 538.034 | 300 |
| 601.322 | 300 |
| 833.515 | 520 |
| 906.143 | 250 |
| 908.851 | 250 |
| 909.483 | 450 |
| 911.18 | 300 |
| 940.573 | 800 |
| 962.08 | 250 |
| 965.844 | 300 |
| 1 069.125 | 300 |

TABLE 3

Oxygen

| Observed Wavelength of Peak | Relative Intensity of Peak |
|---|---|
| 777.194 | 870 |
| 777.417 | 810 |
| 777.539 | 750 |
| 844.625 | 810 |
| 844.636 | 1000 |
| 844.676 | 935 |
| 926.277 | 590 |
| 926.601 | 640 |
| 1 128.691 | 640 |
| 1 316.389 | 700 |
| 1 316.485 | 750 |
| 1 316.511 | 640 |

TABLE 4

Nitrogen

| Observed Wavelength of Peak | Relative Intensity of Peak |
|---|---|
| 575.25 | 700 |
| 742.364 | 685 |
| 744.229 | 785 |
| 746.831 | 900 |
| 859.4 | 570 |
| 862.924 | 650 |
| 868.028 | 700 |
| 868.34 | 650 |
| 871.17 | 570 |
| 939.279 | 570 |
| 1 246.962 | 920 |
| 1 358.133 | 840 |

TABLE 5

Fluorine

| Observed Wavelength of Peak | Relative Intensity of Peak |
|---|---|
| 623.965 | 13000 |
| 634.851 | 10000 |
| 683.426 | 9000 |
| 685.603 | 50000 |
| 690.248 | 15000 |
| 703.747 | 45000 |
| 712.789 | 30000 |
| 720.236 | 15000 |
| 731.102 | 15000 |
| 739.869 | 10000 |
| 775.47 | 18000 |
| 780.021 | 15000 |

TABLE 6

Hydrogen

| Observed Wavelength of Peak | Relative Intensity of Peak |
|---|---|
| 388.9049 | 6 |
| 397.0072 | 8 |
| 410.174 | 15 |
| 434.047 | 30 |
| 486.133 | 80 |
| 656.272 | 120 |
| 656.2852 | 180 |
| 954.597 | 5 |
| 1 004.94 | 7 |
| 1 093.81 | 12 |

TABLE 6-continued

Hydrogen

| Observed Wavelength of Peak | Relative Intensity of Peak |
|---|---|
| 1 281.81 | 20 |
| 1 875.10 | 40 |

TABLE 7

Phosphorous

| Observed Wavelength of Peak | Relative Intensity of Peak |
|---|---|
| 944.186 | 950 |
| 930.494 | 1250 |
| 949.356 | 1250 |
| 952.573 | 1700 |
| 954.518 | 1500 |
| 956.3439 | 1700 |
| 973.475 | 1500 |
| 975.077 | 1500 |
| 979.685 | 1700 |
| 1 052.952 | 962 |
| 1 058.157 | 1235 |
| 1 648.292 | 1627 |

TABLE 8

Iodine

| Observed Wavelength of Peak | Relative Intensity of Peak |
|---|---|
| 511.929 | 10000 |
| 661.966 | 5000 |
| 740.206 | 5000 |
| 746.899 | 5000 |
| 804.374 | 99000 |
| 839.33 | 10000 |
| 902.24 | 5000 |
| 905.833 | 15000 |
| 911.391 | 12000 |
| 942.671 | 4000 |
| 973.173 | 5000 |
| 1 046.654 | 5000 |

TABLE 9

Chlorine

| Observed Wavelength of Peak | Relative Intensity of Peak |
|---|---|
| 725.662 | 7500 |
| 754.7072 | 11000 |
| 771.7581 | 7000 |
| 774.497 | 10000 |
| 821.204 | 18000 |
| 822.174 | 20000 |
| 833.331 | 18000 |
| 837.594 | 99900 |
| 842.825 | 15000 |
| 857.524 | 20000 |
| 858.597 | 75000 |
| 912.115 | 7500 |

TABLE 10

Germanium

| Observed Wavelength of Peak | Relative Intensity of Peak |
|---|---|
| 201.9068 | 1700 |
| 204.1712 | 2400 |
| 204.377 | 1600 |
| 206.5215 | 750 |
| 206.8656 | 2600 |
| 209.4258 | 2000 |
| 265.1172 | 1200 |
| 270.9624 | 850 |
| 275.4588 | 650 |
| 303.9067 | 750 |
| 1 206.920 | 1300 |
| 1 239.158 | 1050 |

TABLE 11

Halfnium

| Observed Wavelength of Peak | Relative Intensity of Peak |
|---|---|
| 286.637 | 2100 |
| 289.826 | 1800 |
| 291.648 | 2000 |
| 294.077 | 2000 |
| 295.068 | 1200 |
| 296.488 | 1400 |
| 302.053 | 1200 |
| 307.288 | 2100 |
| 368.224 | 2200 |
| 377.764 | 1400 |
| 378.546 | 1400 |
| 382.073 | 1300 |

TABLE 12

Gallium

| Observed Wavelength of Peak | Relative Intensity of Peak |
|---|---|
| 639.6561 | 9 |
| 725.14 | 10 |
| 740.3 | 20 |
| 746.4 | 30 |
| 762.05 | 10 |
| 773.477 | 50 |
| 780.001 | 100 |
| 800.255 | 15 |
| 807.425 | 20 |
| 838.649 | 7 |
| 1 194.912 | 10 |
| 1 210.978 | 9 |

As described in detail above, embodiments in accordance with the present invention are particularly suited for implementation in conjunction with a computer. FIG. 12 is a simplified diagram of a computing device for processing information according to an embodiment of the present invention. This diagram is merely an example which should not limit the scope of the claims herein. One of ordinary skill in the art would recognize many other variations, modifications, and alternatives. Embodiments according to the present invention can be implemented in a single application program such as a browser, or can be implemented as multiple programs in a distributed computing environment, such as a workstation, personal computer or a remote terminal in a client server relationship.

FIG. 12 shows computer system 1210 including display device 1220, display screen 1230, cabinet 1240, keyboard 1250, and mouse 1270. Mouse 1270 and keyboard 1250 are representative "user input devices." Mouse 1270 includes buttons 1280 for selection of buttons on a graphical user interface device. Other examples of user input devices are a touch screen, light pen, track ball, data glove, microphone, and so forth. FIG. 12 is representative of but one type of system for embodying the present invention. It will be readily apparent to one of ordinary skill in the art that many system types and configurations are suitable for use in conjunction with the present invention. In a preferred embodiment, computer system 1210 includes a Pentium class based computer, running Windows XP operating system by Microsoft Corporation. However, the apparatus is easily adapted to other operating systems and architectures by those of ordinary skill in the art without departing from the scope of the present invention.

As noted, mouse 1270 can have one or more buttons such as buttons 1280. Cabinet 1240 houses familiar computer components such as disk drives, a processor, storage device, etc. Storage devices include, but are not limited to, disk drives, magnetic tape, solid state memory, bubble memory, etc. Cabinet 1240 can include additional hardware such as input/output (I/O) interface cards for connecting computer system 1210 to external devices, external storage, other computers or additional peripherals, further described below.

FIG. 12A is an illustration of basic subsystems in computer system 1210 of FIG. 12. This diagram is merely an illustration and should not limit the scope of the claims herein. One of ordinary skill in the art will recognize other variations, modifications, and alternatives. In certain embodiments, the subsystems are interconnected via a system bus 1275. Additional subsystems such as a printer 1274, keyboard 1278, fixed disk 1279, monitor 1276, which is coupled to display adapter 1282, and others are shown. Peripherals and input/output (I/O) devices, which couple to I/O controller 1271, can be connected to the computer system by any number of means known in the art, such as serial port 1277. For example, serial port 1277 can be used to connect the computer system to a modem 1281, which in turn connects to a wide area network such as the Internet, a mouse input device, or a scanner. The interconnection via system bus allows central processor 1273 to communicate with each subsystem and to control the execution of instructions from system memory 1272 or the fixed disk 1279, as well as the exchange of information between subsystems. Other arrangements of subsystems and interconnections are readily achievable by those of ordinary skill in the art. System memory, and the fixed disk are examples of tangible media for storage of computer programs, other types of tangible media include floppy disks, removable hard disks, optical storage media such as CD-ROMS and bar codes, and semiconductor memories such as flash memory, read-only-memories (ROM), and battery backed memory.

It is understood that the examples and embodiments described herein are for illustrative purposes only and that various modifications or changes in light thereof will be suggested to persons skilled in the art and are to be included within the spirit and purview of this application and scope of the appended claims

What is claimed is:

1. A computer-implemented method, comprising:
   sampling a gas in molecular form from a process chamber operating at sub-atmospheric pressure;
   applying power to molecules of the gas, such that a significant fraction of optical emissions from a plasma of the gas are from individual atoms of the molecules of the gas resulting from the power being applied to the molecules of the gas; and
   determining, using a processor associated with a computer system, relative concentrations of atoms of the gas based at least in part upon measurements of the optical emissions resulting from the power being applied to the molecules of the gas.

2. The method of claim 1 wherein the power applied is such that an intensity of emission from the atoms is at least 20% of an intensity of emission from the gas in molecular form.

3. The method of claim 1 wherein the power applied is such that an intensity of emission from atomic nitrogen in air at 747 nm is at least 20% of an intensity of emission from molecular nitrogen at 747 nm.

4. The method of claim 1 wherein the power applied is such that an intensity of emission from atomic carbon at 248 nm is at least 20% of an intensity of emission from molecular CO at 520 nm for a plasma etching process where silicon oxide is being etched in a fluorocarbon/oxygen chemistry.

5. The method of claim 1 wherein the power applied is such that an intensity of emission from atomic silicon at 251 nm is at least 20% of an intensity of emission from molecular SiF at 440 nm for a plasma etching process where silicon oxide is being etched in a fluorocarbon/oxygen chemistry.

6. The method of claim 1 wherein the power applied is such that an intensity of emission from atomic F at 686 nm is at least 20% of an intensity of emission from molecular CO at 520 nm in a fluorocarbon/oxygen chemistry.

7. The method of claim 1 wherein the plasma is exposed to a power density of 3 W/cm$^3$ or greater.

8. The method of claim 1 wherein the plasma is exposed to a power density of 5 W/cm$^3$ or greater.

9. The method of claim 1 wherein the plasma is exposed to a power density of 10 W/cm$^3$ or greater.

10. The method of claim 1 wherein the plasma is exposed to a power density 20 W/cm$^3$ or greater.

11. The method of claim 1 wherein the plasma is exposed to a power density of between about 3-40 W/cm$^3$.

12. The method of claim 1 wherein the power is applied continuously.

13. The method of claim 1 wherein the power is applied as a pulse.

14. The method of claim 13 wherein a duration of the pulse is between about 0.5-50 milliseconds.

15. The method of claim 13 wherein the pulse occurs at a frequency of between about once per minute and 20 times per second.

16. The method of claim 1 wherein the gas is sampled from a semiconductor processing chamber.

17. The method of claim 16 further comprising determining an endpoint of a process occurring in the semiconductor processing chamber based upon the relative concentrations of atoms of the gas.

18. A computer implemented method, comprising:
    sampling a gas in molecular form from a process chamber operating at sub-atmospheric pressure;
    exposing molecules of the gas to an RF power having a density of greater than about 3 W/cm$^3$ to form a plasma, such that a significant fraction of optical emissions from the plasma of the gas are from individual atoms of the molecules of the gas resulting from the RF power being applied to the molecules of the gas;
    measuring the optical emissions from the plasma; and
    determining, using a processor associated with a computer system, relative concentrations of atoms of the gas based at least in part upon the measured optical emissions resulting from the RF power exposure of the molecules of the gas.

19. The method of claim 18 wherein the gas is sampled from a processing chamber in which a semiconductor fabrication process is being performed.

20. The method of claim 18 further comprising determining an endpoint of the semiconductor fabrication process based upon the relative concentrations of the atoms of the gas.

21. The method of claim 18 wherein the RF power density is applied as a pulse.

22. The method of claim 21 wherein a duration of the pulse is between about 0.5-50 milliseconds.

23. The method of claim 21 wherein the pulse occurs at a frequency of between about once per minute and 20 times per second.

24. An apparatus comprising:
a chamber configured to receive a gas in molecular form from a process chamber operating at sub-atmospheric pressure;
a power generator configured to apply sufficient RF power to molecules of the gas to create a plasma from the gas, such that a significant fraction of optical emissions from the plasma of the gas are from individual atoms of the molecules of the gas resulting from the RF power being applied to the molecules of the gas, the plasma exposed to a power density of greater than about 3 $W/cm^3$; and
a spectrometer in optical communication with the chamber and configured to measure the optical emissions from the plasma.

25. The apparatus of claim 24 further comprising a processor in electronic communication with the spectrometer, the processor configured to correlate the optical emissions with relative concentrations of gases within the chamber.

26. The apparatus of claim 25 wherein the processor is configured to determine a process endpoint based upon the relative concentrations of atoms in the plasma.

27. The apparatus of claim 24 further comprising a pulse generator in electronic communication with the power generator.

28. An apparatus comprising:
a chamber configured to receive a gas in molecular form sampled from a process occurring at sub-atmospheric pressure;
a power generator configured to apply a radio frequency power to molecules of the sampled gas within the chamber, such that a significant fraction of optical emissions from a plasma of the gas are from individual atoms of the molecules of the gas resulting from the radio frequency power being applied to the molecules of the gas; and
a spectrometer in optical communication with the chamber and configured to measure the optical emissions from the plasma of the gas, wherein,
if the sampled gas is from a plasma etching process where silicon oxide is being etched in a fluorocarbon/oxygen chemistry, an intensity of emission from atomic F at 686 nm is at least 20% of an intensity of emission from molecular CO at 520 nm,
if the sampled gas is from a plasma etching process where silicon oxide is being etched in a fluorocarbon/oxygen chemistry, an intensity of emission from atomic silicon at 251 nm is at least 20% of an intensity of emission from molecular SiF at 440 nm,
if the sampled gas is from a plasma etching process where silicon oxide is being etched in a fluorocarbon/oxygen chemistry, an intensity of emission from atomic carbon at 248 nm is at least 20% of an intensity of emission from molecular CO at 520 nm, or
if the sampled gas is air, an intensity of emission from atomic nitrogen at 747 nm is at least 20% of an intensity of emission from molecular nitrogen at 747 nm.

29. The apparatus of claim 28 wherein the power generator is configured to apply the radio frequency power of at least 100 W.

30. The apparatus of claim 28 wherein the power generator is configured to apply the radio frequency power of at least 200 W.

31. The apparatus of claim 28 wherein the power generator is configured to apply the radio frequency power as a pulse having a duration of between about 0.5 and 50 milliseconds, at a frequency of between about once per minute and 20 times per second.

32. The apparatus of claim 28 not requiring a separate cooling mechanism for the chamber.

33. An apparatus comprising:
a chamber configured to receive a gas in molecular form sampled from a process occurring at sub-atmospheric pressure;
a power generator configured to apply a radio frequency power to a plasma of the gas within the chamber, such that a significant fraction of optical emissions from the plasma of the gas are from individual atoms of the molecules of the gas resulting from the radio frequency power being applied to the plasma of the gas; and
a spectrometer in optical communication with the chamber and configured to measure the optical emissions from the plasma, wherein the power generator is configured to apply the radio frequency power of at least 100 W.

34. The apparatus of claim 33 wherein the power generator is configured to apply the radio frequency power as a pulse having a duration of between about 0.5 and 50 milliseconds, at a frequency of between about once per minute and 20 times per second.

35. The apparatus of claim 33 not requiring a separate cooling mechanism for the chamber.

36. An apparatus comprising:
a chamber configured to receive a gas in molecular form sampled from a process occurring at sub-atmospheric pressure;
a power generator configured to apply a radio frequency power to a plasma of the gas within the chamber, such that a significant fraction of optical emissions from the plasma of the gas are from individual atoms of the molecules of the gas resulting from the radio frequency power being applied to the plasma of the gas; and
a spectrometer in optical communication with the chamber and configured to measure the optical emissions from the plasma, wherein the power generator is configured to apply the radio frequency power of at least 200 W.

37. The apparatus of claim 36 wherein the power generator is configured to apply the radio frequency power as a pulse having a duration of between about 0.5 and 50 milliseconds, at a frequency of between about once per minute and 20 times per second.

38. The apparatus of claim 36 not requiring a separate cooling mechanism for the chamber.

* * * * *